United States Patent
Cohen et al.

(10) Patent No.: US 8,708,952 B2
(45) Date of Patent: Apr. 29, 2014

(54) REMOTELY CONTROLLED CATHETER INSERTION SYSTEM

(75) Inventors: Todd J. Cohen, Port Washington, NY (US); Dara McMahon, Natick, MA (US); Robert C. Royce, Jr., Mansfield, MA (US)

(73) Assignee: Catheter Robotics, Inc., Budd Lake, NJ (US)

( * ) Notice: Subject to any disclaimer, the term of this patent is extended or adjusted under 35 U.S.C. 154(b) by 579 days.

(21) Appl. No.: 12/515,005

(22) PCT Filed: Jan. 16, 2009

(86) PCT No.: PCT/US2009/031357
§ 371 (c)(1),
(2), (4) Date: Jan. 21, 2011

(87) PCT Pub. No.: WO2009/092059
PCT Pub. Date: Jul. 23, 2009

(65) Prior Publication Data
US 2011/0105954 A1    May 5, 2011

Related U.S. Application Data

(60) Provisional application No. 61/021,507, filed on Jan. 16, 2008, provisional application No. 61/052,790, filed on May 13, 2008.

(51) Int. Cl.
*A61M 25/01* (2006.01)
(52) U.S. Cl.
USPC .......................... 604/95.01; 600/434; 604/263
(58) Field of Classification Search
USPC ............ 600/585, 114, 434; 604/95.01–95.05, 604/263, 28, 529
See application file for complete search history.

(56) References Cited

U.S. PATENT DOCUMENTS

| 4,549,538 A | 10/1985 | Schadrack, III et al. |
| 4,721,123 A | 1/1988 | Cosentino et al. |

(Continued)

FOREIGN PATENT DOCUMENTS

| JP | 2007527296 A | 9/2007 |
| WO | 2007/008967 A2 | 1/2007 |

(Continued)

OTHER PUBLICATIONS

International Preliminary Report on Patentability, Intl. Application PCT/US2009/031357. International Bureau of WIPO, Jul. 29, 2010.

(Continued)

*Primary Examiner* — Max Hindenburg
*Assistant Examiner* — John Pani
(74) *Attorney, Agent, or Firm* — The Marbury Law Group, PLLC

(57) ABSTRACT

A system for remotely controlling the positioning within the body of a patient of an elongated medical device optionally having a control handle, comprises a robotic system and a remote controller configured to control the robotic device. The robotic system comprises a handle controller; a sled member coupled to the handle controller, the sled member being configured to position the medical device within the body of the patient; and a sled base configured to advance the sled member towards the body of a patient, the sled bed being coupled to a sterile barrier effective to maintain sterility inside the sled base. A medical device introducer is effective to guide the elongated medical device into a patient's body.

45 Claims, 24 Drawing Sheets

(56) References Cited

U.S. PATENT DOCUMENTS

| | | | |
|---|---|---|---|
| 6,096,004 | A | 8/2000 | Meglan et al. |
| 6,398,755 | B1 | 6/2002 | Belef et al. |
| 6,445,984 | B1 | 9/2002 | Kellogg |
| 7,758,564 | B2 | 7/2010 | Long et al. |
| 8,046,049 | B2 | 10/2011 | Govari et al. |
| 2002/0183723 | A1* | 12/2002 | Belef et al. .................. 606/1 |
| 2004/0254566 | A1 | 12/2004 | Plicchi et al. |
| 2005/0038412 | A1 | 2/2005 | Rabiner et al. |
| 2007/0016174 | A1 | 1/2007 | Millman et al. |
| 2007/0233044 | A1 | 10/2007 | Wallace et al. |
| 2007/0283263 | A1* | 12/2007 | Zawde et al. .................. 715/700 |
| 2007/0299479 | A1* | 12/2007 | Saksena .................... 607/18 |
| 2008/0009791 | A1* | 1/2008 | Cohen et al. ............... 604/95.01 |
| 2010/0256558 | A1* | 10/2010 | Olson et al. ............... 604/95.01 |
| 2012/0197182 | A1* | 8/2012 | Millman et al. ............ 604/24 |
| 2012/0220931 | A1 | 8/2012 | Cohen et al. |

FOREIGN PATENT DOCUMENTS

| | | |
|---|---|---|
| WO | 2007008967 A2 | 1/2007 |
| WO | 2009092059 A3 | 7/2009 |

OTHER PUBLICATIONS

International Search Report and Written Opinion, Intl. Application PCT/US2009/031357. International Search Authority: U.S. Patent and Trademark Office (ISA/US), May 19, 2009.

Extended European Search Report of Apr. 17, 2013; European Application No. 09702983.9.

Japanese Patent Application No. 2010-543298; Office Action of Mar. 19, 2013.

Chinese Application 200680025512.7, State Intellectual Property Office of the People's Republic of China, Office Action dated Feb. 13, 2012.

Chinese Application 200980102420.8, State Intellectual Property Office of the People's Republic of China, Office Action dated Feb. 16, 2012.

U.S. Appl. No. 13/051,736, Non-Final Office Action dated Jul. 17, 2012.

U.S. Appl. No. 12/903,397, Non-Final Office Action dated Nov. 19, 2012.

U.S. Appl. No. 13/051,736, Final Office Action dated Nov. 5, 2012.

Canadian Application 2,646,846, Office Action dated Sep. 19, 2012.

* cited by examiner

REMOTELY CONTROLLED CATHETER INSERTION SYSTEM

CROSS-REFERENCE TO RELATED APPLICATIONS

This application is a U.S. National Stage Entry of International Patent Application No. PCT/US09/31357 filed in Jan. 16, 2009, which claimed the benefit of priority to U.S. Provisional Patent Application Ser. No. 61/021,507, filed Jan. 16, 2008, and U.S. Provisional Patent Application Ser. No. 61/052,790, filed May 13, 2008, each of which is hereby incorporated herein by reference in its entirety.

FIELD OF THE INVENTION

The present invention is directed to the positioning of medical devices within the body of a patient. More particularly, the invention is directed to the positioning of medical devices such as catheters within a patient's body using a remotely controlled system wherein the delivery of the catheter is conducted through sterile means. Alternatively, the invention can also be used to position and deploy pacemaker and/or defibrillator leads.

BACKGROUND

Invasive procedures, such as invasive electrophysiology procedures, are very complicated and presently require the use of radiation, e.g., fluoroscopy, to visualize the location of a device such as a catheter and to help position the device within a patient's body at a site, such as the heart or the circulatory system. To facilitate catheter placement, certain fields, including the field of electrophysiology, have developed multi-poled and shaped steerable catheters. In addition, three-dimensional non-fluoroscopic mapping systems have also been developed to help identify catheter locations in space and to document their locations along with the electrical activity of the heart.

Even with the advent of such catheters and mapping systems, these procedures still can expose the patient, operator, and other staff to high cumulative dosages of radiation which may have long term adverse effects on those exposed. A patient may be directly exposed only once or twice to such procedures; however, a high volume operator and staff can be exposed both directly and indirectly to the radiation during many procedures over a long period of time.

To protect the operator and staff from this radiation, shielding comprising lead aprons, gowns, glasses, skirts, etc., is worn. Such lead clothing, especially a lead apron, is quite heavy and uncomfortable, and its use has been associated with cervical and lumbar spine injury.

An alternative to this lead shielding is "imitation" lead, i.e., lead-like substances used as barriers. Even this lighter weight shielding still applies continuous force to the spinal column which can result in discomfort and neck, back, and/or sacral spine injury over time.

In view of the concerns regarding radiation exposure and the drawbacks of lead protection, techniques and systems have been developed so that a physician or technician may be able to control the insertion and movement of a catheter remotely. Commercially available catheters, such as balloon dilatation angioplasty catheters, typically have at least six ranges of motion. Known systems for remote control of catheters require the use of specialized catheters compatible with a particular system. The specialized catheters are more expensive than the commercially available, off the shelf catheters. Also, the known remotely controlled catheter insertion systems have controls that are not intuitive and do not conform to procedures generally taught in medical school. As a consequence, a user is required to learn a new device and new movement controls for insertion of the catheter.

Thus, there is a need for a remotely controllable catheter insertion system which can utilize commercially available catheters and take advantage of the known features of such catheters. This will enable the user to utilize the device using a control input which is comfortable and familiar to the user.

In prior systems of delivering a catheter to a patient, enclosures have prevented the operator from manually adjusting the catheter when necessary. The present invention permits an operator to manually adjust the catheter in the catheter holder even when the insertion system is in operation.

SUMMARY OF THE INVENTION

According to the invention, a system and method are provided for remotely controlling a robotic device to insert and position a medical device such as a catheter within the body of a human or animal patient. The device can be visualized by use of standard fluoroscopy (with X-rays), cine angiography, and/or three-dimensional mapping non-fluoroscopic imaging modalities, which can have direct and/or remote monitoring capabilities or otherwise. Certain embodiments of the invention allow an operator, such as a doctor or another medical professional, to be positioned at a location that is remote from the actual location of a patient, and to use a remote control mechanism comprising a remote control station and a controller to control a robotic device to insert, place, and position medical devices such as catheters within the body of the patient. The catheter may be fed into a nonvascular part of the body to find a target and record, diagnose, and/or deliver treatment or therapy. The catheter may be positioned on a delivery device disposed on a mechanical delivery system which maintains the sterility of the catheter prior to and during insertion into the patient. A system may integrate an imaging modality with a remote monitor, and the medical device may be positioned in the body by remotely visualizing the medical device. The device may then be positioned using a system as discussed above.

In one embodiment of the invention, venous or arterial vascular access or nonvascular access is performed directly by an operator, and a medical device such as a catheter is inserted into an introducer sheath and then fed and advanced and steered through a sterile environment to the appropriate location. In another embodiment of the invention, the operator of the medical procedure can advance, remove, shape, steer, and deflect a standard electrophysiology catheter, such as an ablation catheter, within the patient from a location remote from the patient, such as a shielded control room, and avoid exposure to potentially harmful radiation normally associated with such a procedure. In this manner, the present invention may eliminate the need for doctors or other medical personnel to wear protective gear in performing such medical procedures. Such protective gear may be uncomfortable, less than fully effective, and cause injury to the wearer over time.

In another embodiment of the invention, a system and method of controlling a robotic device for positioning a medical device, such as a catheter, within the body of a patient is provided. The medical device is an elongated medical device having a control handle, examples of which include catheters, guide wires, introducer sheaths or catheters, and guide sheaths or catheters. Examples of specific catheters include, but are not limited to, ablation catheters, mapping catheters, balloon dilatation catheters, perfusion catheters, pacing and/ or defibrillation leads, and the like. This embodiment may comprise a robotic device configured to position the medical device within the body of the patient and a remote control mechanism or system configured to control the robotic device to position the medical device. The remote control mechanism preferably comprises (1) a remote control station and (2) a controller in communication with the remote control station. Preferably the robotic device has a handle controller to receive the control handle of the medical device and the robotic device is coupled to a sled member for advancing said catheter. The remote control mechanism may comprise a remote control station and a robotic device controller wherein an operator, such as a doctor or another medical professional, uses the remote control station to control the robotic device. The remote control station comprises appropriate control knobs, levers, switches, buttons, slides, or other controls, such as a joystick. The handle controller of the robotic device is coupled to a mobile sled member that advances, for example, in two-dimensional linear movement along the rail or rails of a sled bed or base, which sled base may be mounted to a fixed surface or support. The tip of an elongated medical device is inserted through a sterile environment within a sled base prior to and during delivery to a patient to provide maximum sterility. Preferably the robotic device comprises a sterile environment such that, after the elongated medical device is inserted into the patient, the handle can be disengaged from the control, manipulated manually, and then re-engaged with the controller, without breaking sterility.

When manipulated by hand, modem catheter devices are capable of moving in up to six ranges of motion. For example, catheters can clearly be moved forward and backward so that a longer portion of the catheter may be inserted into a subject and removed. Catheters may also be rotated clockwise and counterclockwise. Moreover, the distal end or tip of many catheters, referred to as "steerable," can be deflected in several directions.

The remote control mechanism may also include one or more transmitters, receivers, or transceivers to communicate information between the remote control station and the robotic device controller, by any wired and/or wireless transmission mechanism, including via dial-up, cable, or broadband modem internet transmission. The operator may control the robotic device from a location that is remote from the location of the patient, including, but not limited to, a shielded control room. The robotic device may include one or more sensors to communicate information to the remote control station regarding movement of the catheter and the environment of the catheter within the patient's body. More particularly, the handle controller can be hard-wired or wireless, the handle controller providing HAPTIC (i.e., feel) feedback through a resistive, vibratory, sound, and or color-coded LED mechanism. Similarly, the robotic device may have sensors that provide desired information, such as force, pressure, temperature, or location, to the control station or the remote controller.

In another embodiment of the invention, the robotic device may be configured to allow the operator to insert the medical device within the body of the patient and position the medical device within the body of the patient. The medical device may be a catheter, and the robotic device may be a catheter control device configured to allow the operator, using the remote control device, to do one or more of the following within the patient's body: insert the catheter, advance or feed the catheter, steer the catheter, rotate the catheter, place the catheter, shape the catheter, or deflect the catheter. The catheter or other medical device may be inserted into and positioned within a variety of portions and systems of the patient's body, such as within the heart or the circulatory system of the patient.

In another embodiment of the invention, the elongated medical device may be a catheter, such as an electrophysiology catheter and/or an interventional catheter. The catheter or other medical device may be used for a cardiac, vascular, radiological, gastroenterological, or nephrological procedure or for a combination of two or more such procedures, and it may optionally be used to deliver therapy for such procedures, including the delivery of biologicals such as stem cells, angiogenesis factors, etc. The catheter may also be used for mapping, catheter ablation, stenting, angioplasty, atrial fibrillation ablation, ventricular tachycardia ablation, and/or other complex forms of catheter ablation (e.g., multiple atrial tachycardias, etc.), or delivery of drugs or medicine, or a combination of two or more of such procedures.

In another embodiment of a robotic insertion device of the invention, a standard steerable catheter or elongated medical device having a tip can be inserted into a human body and then the steerable catheter or medical device can be manually disengaged from the handle controller of the robotic insertion device and then manually manipulated, while maintaining sterility without dislodging and/or removing the tip's location from inside the human body. The catheter or medical device can easily re-engage the robotic insertion device while continuing to maintain sterility and without dislodging or displacing the tip from its position within the body.

In another embodiment of the invention, a robotic device comprises a handle control assembly/rotary modular plate coupled to a linear sled, which sled member is adapted to secure an elongated medical device such as a catheter to a modular plate. The modular plate may comprise one or more clamps and a molded nest to secure the catheter. In a further embodiment of the invention, the molded nest may be sterilizable or resterilizable. Optionally the molded nest may be disposable. The device may be designed to avoid hard wiring the modular plate. For example, contacts may be used to electrify the motor and deflect the tip. The handle control assembly/rotary modular plate may include an outer housing assembly with means for rotating said medical device, and a means for one or more of shaping, deflecting, steering, placing, or positioning the medical device within the patient.

In another embodiment of the invention, there can be sterile rapid removal and replacement of a catheter without displacing its distal end (tip) and position within the heart and or circulatory system (and/or body). Similarly, there can be rapid sterile replacement back in the robotic system without dislodging, moving the catheter's position within the heart and/or circulatory system (and/or body). The step-by-step process would include putting on sterile gloves, disengaging a catheter from a handle controller, and gingerly removing the catheter body from sled with feeder passively sitting proximally on catheter.

In another embodiment of the invention, the catheter can be advanced and/or manipulated manually.

In another embodiment of the invention, a catheter body in sterile sled can be replaced (has the feel like a zip lock bag) and the handle adjusted to a controlling nest to the position for catheter handle, wherein the handle is replaced in the robot and then returned to the remote mechanism for remote catheter manipulation.

In another embodiment of the invention, a standard catheter or medical device can be rapidly removed from the robotic system without displacing the tip of said catheter and or device from its position within the heart (and/or body).

A significant feature of the invention is that standard, that is, commercially available, catheters and other elongated medical devices such as sheaths or leads are inserted by the robotic insertion system of the invention. Therefore, the robotic insertion system manipulates these catheters and other medical devices without interfering with or otherwise changing the characteristics or safety features of the catheters and other medical devices. The molded nest of the handle controller can support a variety of different catheters, sheaths, or other medical devices designed for different purposes. The same mating nest can be used so long as the handles of the different catheters, sheaths, or other medical devices have the same configurations and controls. For example, Boston Scientific has a number of different mapping and ablation catheters having a handle based upon the handle of the BLAZER™ catheter. There is a design for a LASSO TK style catheter (available from Biosense Webster) used for pulmonary vein mapping, a 20-poled catheter used for right atrial and coronary sinus mapping, and a 4-poled ablation catheter, all with the same handle which will work with the same molded nest.

In another embodiment of the invention, the sled member may be coupled to a sled base with means of advancing the sled member backwards and forwards along a rail system. Optionally the sled base further comprises a sterile barrier sealing the rail system. The movement may be two-dimensional, that is, back and forth. However, the movement may be non-linear, such as arcuate or otherwise curved, even circular, or a combination or linear and curved.

In another embodiment of the invention, the sled base is elongated with a distal end and a proximal end. The sled base comprises two rails which extend parallel to the edges of said sled base along its entire length. A motor effective for advancing the sled member may be found at the proximal end of the sled base. In another embodiment of the invention, a first rail contains a threaded screw drive coupled to a linear sled. A second rail comprises a slotted flexible extrusion, effective to receive a catheter or sheath. Preferably said slotted flexible extrusion is sterile.

A catheter, for example, positioned in a molded nest on the modular plate of the sled base, may be remotely deflected to a position, such that the distal end of the catheter penetrates the sterile barrier of the sled base. In this embodiment, when the device is operating, the distal end of the catheter is advanced within the sterile environment within the sled base. The sterile barrier separates the catheter or sheath from the system to provide sterility and further provides a track to guide the catheter along the rail. Optionally the sterile barrier comprises lips or flaps to seal and reseal the rail.

The rails are sealed with a sterile guide barrier which, in an embodiment, run parallel to the bottom of said sled base. In another embodiment of the invention, the sterile guide barrier is a split flexible tube with a flexible wiper configuration through which the elongated medical device is easily inserted. The sterile guide is inserted with a snap fit into a channel running along the length of the sled base. Optionally the sterile guide barrier is disposable.

In another embodiment of the invention, the sterile guide barrier separates the catheter or sheath from the system for sterility and guides the catheter along the linear sled. The distal end of the sterile guide barrier cantilevers at the end of the sled base through a system coupling, and its terminal end is connected to the catheter introducer.

In another embodiment of the invention, the cantilevered sterile guide barrier and flexible system coupling transition the catheter from a rigid movement along the guide barrier receiver to a compliant connection with the introducer coupling to facilitate effective catheter placement.

In another embodiment of the invention, for the catheter to travel through the sterile guide barrier, rotary modular plate/handle controller, it is necessary that it is mounted on the sled member on an angle and that the proximal end of the catheter is rigidly nested to prevent buckling and guide the catheter along the sterile guide barrier. In this embodiment, the catheter is coupled to a feeder at the proximal end of the catheter. The feeder is attached to the catheter by a feeder support. The catheter is deflected downwards towards the lips of the sterile barrier, and the feeder is effective to separate the lips of the sterile barrier at the location of contact. The catheter tip is subsequently inserted into the sterile barrier. Optionally the sterile barrier may be disposed of after use.

The feeder spreads the sterile barrier as the proximal end of the catheter or sheath moves along the sled base. The sterile barrier opens along the leading edge and, at the same time, closes on the trailing edge. In another embodiment of the invention, the feeder spreads the sterile guide barrier as the proximal end of the catheter or sheath moves along the sled base. In a further embodiment of the invention, the sterile guide barrier incorporates a flexible wiper design that causes the split tube of the sterile guide barrier to open along the leading edge of the moving catheter or sheath and at the same time to close the opening of the trailing edge to preserve sterility.

In a further embodiment of the invention, a sterile poly bag is used to seal the sled base to keep the sled base sterile. The poly bag has an elastic band that stretches along the length of the sterile barrier and allows the sled of the device to slide along the path without binding the poly bag. Preferably the poly bag maintains a sterile environment between the device and the patient. Optionally the sterile poly bag may be disposed of after use.

In another embodiment of the invention, the sled base further comprises an introducer coupling located at the distal end of the sled base, the introducer coupling being effective to introduce the catheter or sheath into the patient's body. The catheter or sheath travels down the rail, and, at the proximal end of the sled base, the catheter or sheath interfaces with the introducer coupling which directs the catheter or sheath into the body of the patient.

In another embodiment of the invention, the sled base comprises an inner nose cone at the distal end of the sled base. The inner nose cone maintains a sterile environment between the interior of the sled base bounded by the sterile barrier and the exterior environment. Preferably the inner nose cone is sterile and is permanently attached to the sled base. Optionally the inner nose cone may be disposed of after use.

In another embodiment, the inner nose cone may be coupled to an outer nose cone. The outer nose cone completely covers the inner nose cone to maintain a sterile environment inside the sled base bounded by the sterile barrier. Preferably the outer nose cone is further adapted to clamp the aforementioned introducer. Optionally the outer nose cone is disposable after use. The inner nose cone and/or the outer nose cone operate to prevent buckling of the elongated medical device.

In another embodiment of the invention, the remote control station may comprise a joystick. In a further embodiment of the invention, a computer-guided navigation system may be employed with a similar or equivalent catheter introducer system with sensor feedback to translate the actual resistance to movement, tip pressure, and catheter motion which is occurring in the body to the remote catheter introducer system/model. A human model with traditional sheath and catheter appearance, with sensors, can serve as the controller translating information to the handle control device and feeder system. This set up could allow the operator to insert and manipulate a catheter by standard fashion, remotely and transmit and manipulate an interventional catheter within the human body.

The remote control mechanism may optionally include an apparatus or model in which a catheter is introduced or manipulated, similar to that which is inserted into the human body. That catheter and model control mechanism can transmit information back and forth to the catheter handle control device and catheter feeder system so as to translate manipulation, performed remotely to the actual invasive system. Sensors and registers exist in the model (remote control mechanism) to convey the actual feel of the invasive catheter to that of the catheter model remote controller. In another embodiment of the invention, the apparatus or model resembles the human anatomy for catheter insertion. Such a model can comprise an introducer sheath; a catheter and handle and gears; and sensors, resistors, and transistors. In another embodiment of the invention, when integrated with imaging modalities such as 3D mapping, the remote control is a computer in which catheter translations, movement/manipulations, can be remotely performed (possibly automatically with the ability for human intervention and/or input) by safe iterative steps in order to safely reach targeted sites for catheter deployment.

In another embodiment of the invention, handles, knobs, and/or switches on a catheter handle are manipulated as the remote control is translated into precise movement and feel of a similar catheter which is inserted and manipulated robotically within the human body.

In a further embodiment of the invention, a robotic device comprises a handle controller effective to receive or replicate the control handle of a medical device, the medical device having at least three ranges of motion and a distal end; a first motor in communication with the handle controller and capable of moving the medical device in the axial direction; a second motor in communication with the handle controller and capable of rotating the distal end of the medical device; a third motor in communication with the handle controller and capable of deflecting the distal end of the medical device; and a control unit communication with the first, second, and third motors.

In a further embodiment of the invention, the first motor is connected to an externally threaded drive screw, the handle controller is connected to an internally threaded drive support, and the drive screw is mated with the drive support. The sled member is propelled along the sled base through the motions of the threaded screw drive.

In another embodiment of the invention, there can be more or less than three motors. In addition, there can be a back end unit to control a second medical device such as, for example, a catheter, stylet, or guide wire. For example, the first component system may control a steerable sheath, and a second, back end system or controller may control a steerable catheter. Thus, there can be a plurality of controllers to achieve additional maneuverability.

In a further embodiment of the invention, the third motor is connected to the knob through a first, second, and third gears, the third gear including a gear extension defining an opening for the knob.

In a further embodiment of the invention, the control unit is connected to the first, second, and third motors through the use of wires.

In a further embodiment of the invention, the control unit is connected to the first, second, and third motors wirelessly.

In a further embodiment of the invention, the control unit includes a separate control for each of the first, second, and third motors.

In a further embodiment of the invention, in a system for remotely controlling the positioning of an elongated medical device within the body of a patient, the system comprises a robotic device configured to position the medical device within a body of a patient. The robotic device comprises a handle controller effective to manipulate any control on the handle of the medical device, a driver effective to move the medical device forward and backward, and a catheter feeder effective to deliver the medical device inside the body. The system further includes a remote control mechanism effective to control the robotic device.

The invention further improves the reliability of the system and reduces manufacturing costs through improvements in the deflection and rotational motion drives. The medical device deflection system has an additional motor, belt, pulley and pulley/cam design. The mechanism is housed in the rotating portion of the hand controller. In an embodiment, the pulley/cam drives the interface knob which in turn controls catheter deflection through movement of the knob.

The handle controller may be configured to the shape of a specific catheter. The handle controller may be configured to control features of the catheter to change its shape and contour and to deflect the catheter. The catheter insertion tube is separated from the system for manual intervention during the procedure and to maximize the extent to which the catheter can be inserted into the patient.

The handle controller is coupled to a sled member, which sled member is mounted on a sled base to enable the sled member to move linearly along the length of the sled base. The sled base has a proximal end and a distal end and in one embodiment, has two rails which run the length of the sled bed. The sled member is configured to fit and move above the rail or rails in a manner such that the sled member may be advanced remotely via remote control or manually along the length of the sled bed along the rail or rails to feed out the desired catheter length. In another embodiment of the invention, the sled base is covered by a thin sterile barrier. The sterile barrier may be a sterile poly bag. The poly bag has an elastic band that stretches along the length of the sterile barrier so that the sled of sled member of the device can slide along the path without binding the poly bag. In one embodiment, the poly bag will dress the entire device and act as a barrier between the patient and the device.

The may be disposed at a downward angle to the rail or rails of the sled base. In another embodiment of the invention, the catheter feeder may be coupled to a feeder which is located at the distal end of the handle controller. The feeder spreads the sterile barrier so that a catheter, for example, may be inserted into a slotted flexible extrusion which runs along the length of the rail. The slotted flexible extrusion comprises an aperture through which a catheter is run.

In another embodiment of the invention, the sled base further comprises an inner nose which is attached to the distal end of the sled base. The inner nose cone may be adapted to accept the catheter. Preferably the inner nose cone may be sterilized prior to attachment to the sled base. Optionally the inner nose cone and sterile barrier may be disposed of after use.

A outer nose cone adapted to completely cover the inner nose cone and cover the main rail may be attached to maintain the sterile field of the rail and inner nose cone. The outer nose cone may be detached without touching the inner nose cone. The outer nose cone further comprises an introducer clamp which is adapted to securely latch a catheter introducer such as a sheath. The catheter advanced through the slotted flexible extrusion runs through the introducer before being inserted into the patient's body. The catheter could be placed at locations including the right atrium, the right ventricle, the left atrium, the left ventricle, the endocardium of the heart, the epicardium of the heart, etc.

In a further embodiment of the invention, the remote control mechanism comprises a remote control station and a robotic device controller, with the system configured such that an operator using the remote control station can control the robotic device.

In a further embodiment of the invention, the remote control mechanism includes one or more transmitters, receivers, and/or transceivers to communicate information between the remote control station or remote controller and the robotic device.

In a further embodiment of the invention, the robotic device is controlled from a remote control station or remote controller at a location that is remote from the location of the patient, such as a shielded control room.

In a further embodiment of the invention, the handle controller is modular.

In a further embodiment of the invention, the modular handle controller is designed specifically to receive and manipulate a particular type or model of medical device.

In a further embodiment of the invention, the modular handle controller is designed specifically to control a particular catheter handle and its controls.

In a further embodiment of the invention, the modular handle controller is designed specifically to control delivery, positioning, and placement of a pacemaker and/or defibrillator lead.

In another embodiment of the invention, the handle controller can be adapted to conform to a variety of different elongated medical devices.

In a further embodiment of the invention, the handle controller of the robotic device engages the control handle of a catheter.

In a further embodiment of the invention, the handle controller uses the standard features of the catheter control handle to, within the body of the patient, insert the catheter, steer the catheter, rotate the catheter, place the catheter, shape the catheter, or deflect the catheter, or a combination of two or more thereof.

In a further embodiment of the invention, the catheter is used for mapping and catheter ablation.

In a further embodiment of the invention, the catheter is used for stenting, angioplasty, or drug delivery or a combination of two or more thereof.

In a further embodiment of the invention, the handle controller further includes a catheter feeder system.

In a further embodiment of the invention, the handle controller further comprises a clamp; a handle assembly; and a catheter control assembly.

In a further embodiment of the invention, the handle controller further comprises: an outer housing assembly, wherein the outer housing assembly includes an outer ring and one or more gears; and a clamp assembly effective to clamp the control handle of the medical device to the handle controller, wherein the clamp assembly includes one or more clamp brackets, clamps, or belts.

In a further embodiment of the invention, handle assembly includes a handle outer housing assembly comprised of an outer ring and one or more gears.

In a further embodiment of the invention, the handle controller further comprises means for holding said catheter firmly; means for rotating said catheter; and means for shaping, deflecting, steering, placing, or positioning the catheter, or a combination of two or more thereof, within the patient.

In a further embodiment of the invention, the handle controller further includes one or more sensors to communicate information to the remote control device regarding movement of the catheter and the environment of the catheter within the patient's body.

In a further embodiment of the invention, the information is communicated to the remote station.

In a further embodiment of the invention, the remote control mechanism comprises information regarding manual introduction or manipulation of a catheter into the human body, and the control mechanism can transmit information back and forth to the catheter handle control device and catheter feeder system se-as-to translate manipulation, performed remotely to the actual invasive system.

In a further embodiment of the invention, the remote control comprises a computer in which catheter movement and manipulations can be remotely performed by safe iterative steps to safely reach targeted sites for catheter deployment.

In a further embodiment of the invention, the iterative steps are performed with human oversight.

In a further embodiment of the invention, the handles, knobs, switches, or controls on a catheter control handle are manipulated by the handle controller to approximate the precise movement and feel of a similar catheter which is inserted and manipulated manually within the human body.

In a further embodiment of the invention, a system is securely affixed to a base or support so that a medical device can be delivered to a patient in a stable, predictable, and secure manner.

In a further embodiment, the base or support is a sled member adapted to be advanced on a sled base.

In an embodiment the sled base is mounted with a mounting arm to a firm surface. The mounted sled base may be disposed at an angle to the patient's body.

In a further embodiment of the invention, the mounting arm is mounted to a ceiling, table, wall, floor, tripod, or cart with locking wheels.

In a further embodiment of the invention, the elongated medical device is a pacemaker and/or defibrillator lead.

In a further embodiment of the invention, the robotic device can advance and remove a lead and/or rotate the lead clockwise and counter-clockwise.

In a further embodiment of the invention, a system also includes means for securing and/or deploying a lead for pacing or shocking, i.e., cardioverting or defibrillation, within the coronary sinus vein or its branches.

In a further embodiment of the invention, a lead capable of applying low and/or high voltage therapy to the left atrium or the left ventricle is deployed.

In a further embodiment of the invention, the medical device is a guide wire or stylet.

In a further embodiment of the invention, the robotic device can advance and remove the guide wire or stylet and/or rotate the guide wire or stylet clockwise and counter-clockwise.

In a further embodiment of the invention, the electrophysiology catheter is a mapping and/or ablation catheter.

In a further embodiment of the invention, a system can be used to perform atrial fibrillation ablation.

In a further embodiment of the invention, a system can be used to perform ventricular tachycardia ablation.

In a further embodiment of the invention, a system can be used to perform atrial flutter ablation.

In a further embodiment of the invention, a system can be used to perform atrial tachycardia ablation.

In a further embodiment of the invention, a system can be used to perform pulmonary vein isolation.

In a further embodiment of the invention, a system can be used to perform simple ablations or complex ablations.

In a further embodiment of the invention, a system can be used to perform complex ablations for accessory pathway mediated tachycardias.

In a further embodiment of the invention, a system has limiters to limit the advancement or withdrawal of a medical device.

In a further embodiment of the invention, the medical device is a commercially available steerable catheter, introducer sheath, pacing and/or defibrillation lead, guide wire, or stylet.

In a further embodiment of the invention, in an improved method of mapping, tracking, or delivering therapy with a medical device in combination with an imaging technique, the improvement comprises using a remote positioning control system of the invention to position the medical device.

In a further embodiment of the invention, in an improved method for mapping and catheter ablation by inserting a mapping and ablation catheter into a patient, the improvement comprises using a remote positioning control system of the invention to position the catheter.

In a further embodiment of the invention, a pacing and/or defibrillation lead is placed, deployed, and/or screwed in.

In a further embodiment of the invention, a pacing and/or defibrillation lead is remotely delivered to the right atrium, left atrium, right ventricle, or left ventricle.

In a further embodiment of the invention, a lead is delivered epicardially, endocardially, or via the coronary sinus vein.

In a further embodiment of the invention, a system for remotely controlling the positioning of an elongated medical device within the body of a patient, comprises: a robotic device configured to position the elongated medical device within a body of a patient and a remote control mechanism-effective to control the robotic device. The robotic device comprises a handle controller effective to manipulate any control on the medical device; a driver effective to move the medical device forward and backward; and a catheter feeder effective to deliver the medical device inside the body.

In a further embodiment of the invention, the handle controller is modular, and each module is adaptable to a particular type of medical device.

In a further embodiment of the invention, the handle controller is adaptable to a variety of medical devices.

In a further embodiment of the invention, a system for remotely controlling the positioning within the body of a patient of an elongated medical device having a control handle, comprises:

a medical device feeder effective to maintain the sterility of the medical device and further effective to guide the medical device;

a sled member coupled to a controller device configured to position the medical device within the body of the patient;

a sled base configured to advance the sled member along a rail towards the body of a patient, said sled bed coupled to a sterile barrier, said sterile barrier effective to maintain the sterility inside said sled base by means of a resealable delivery channel effective to receive and guide the catheter, said sled base coupled to an adjustable arm effective to move the sled bed;

a remote control mechanism configured to control the robotic device; and a medical device introducer effective to guide the medical device into a patient's body.

In a further embodiment of the invention, the sled member is equipped with sensors effective to gauge force.

In a further embodiment of the invention, the sensors are positioned on the front, rear, or front and rear of the linear sled.

In a further embodiment of the invention, there is a display wherein colored lights are emitted to indicate the force of the linear sled.

In a further embodiment of the invention, the sensors may emit a sound to indicate force.

In a further embodiment of the invention, the resealable delivery channel comprises a pair of resealable lips.

In a further embodiment of the invention, the medical device feeder has a conically tapered lumen.

In a further embodiment of the invention, the medical device feeder is disposable.

In a further embodiment of the invention, the medical device feeder is sterilizable.

In a further embodiment of the invention, the sled base is covered by a sterile drape effective to maintain sterility and further effective to permit sterile placement of the controller device and sled member onto the sled base without contamination.

In a further embodiment of the invention, a mechanical mount is coupled to the sled base.

In a further embodiment of the invention, the mount is attached to a fluoroscopy table.

In a further embodiment of the invention, the mount may be controlled remotely by an operator using a remote control.

In a further embodiment of the invention, the remote control mechanism comprises a remote control station and a controller device controller, an operator using the remote control station to control the controller device.

In a further embodiment of the invention, the remote control mechanism includes one or more transmitters, receivers, and/or transceivers to communicate information between the remote control station and the controller device controller.

In a further embodiment of the invention, the controller device is controlled from a remote control station at a location that is remote from the location of the patient.

In a further embodiment of the invention, the location of the remote control station is a shielded control room.

In a further embodiment of the invention, the remote control station comprises a joystick that can be an operated by an operator to control the robotic device.

In a further embodiment of the invention, the controller device is further configured to insert the medical device within the body of the patient.

In a further embodiment of the invention, the medical device is a catheter and the robotic device comprises a catheter control device.

In a further embodiment of the invention, a handle controller of the robotic device engages the control handle of the catheter or other elongated medical device.

In a further embodiment of the invention, the handle controller uses the standard features of the catheter control handle to, within the body of the patient, insert the catheter, steer the catheter, rotate the catheter, place the catheter, shape the catheter, or deflect the catheter, or a combination of two or more thereof.

In a further embodiment of the invention, the catheter is an electrophysiology catheter.

In a further embodiment of the invention, the catheter control device is further configured to feed the catheter within the patient's circulatory system.

In a further embodiment of the invention, the catheter is used for a cardiac, vascular, radiological, gastroenterological, or nephrological procedure or for a combination of two or more of such procedures.

In a further embodiment of the invention, the catheter is an interventional catheter used to deliver therapy for the one or more procedures.

In a further embodiment of the invention, the catheter is used for mapping and catheter ablation.

In a further embodiment of the invention, the catheter is used for stenting, angioplasty, or drug delivery or for a combination of two or more thereof.

In a further embodiment of the invention, the sled member further comprises:

a disposable or sterilizable modular plate effective to receive a medical device and further effective to attach the sled member to the handle controller;

at least one clamp to effectively secure said medical device; and a medical device control assembly.

In a further embodiment of the invention, the modular plate is sterilizable or resterilizable.

In a further embodiment of the invention, the modular plate is disposable.

In a further embodiment of the invention, the sled base further comprises:

a guide for guiding the linear sled;

means for maintaining a sterile environment inside the sled base; and means for altering the vertical and/or horizontal orientation of said sled base.

In a further embodiment of the invention, the remote control mechanism comprises information regarding manual introduction or manipulation of a catheter into the human body, and the control mechanism can transmit information back and forth to the catheter handle control device and catheter feeder system so as to translate manipulation, performed remotely to the actual invasive system.

In a further embodiment of the invention, the remote controller comprises a computer in which catheter movement and manipulations can be remotely performed by safe iterative steps to safely reach targeted sites for catheter deployment.

In a further embodiment of the invention, the system is securely affixed to a base or support so that a medical device can be delivered to a patient in a stable, predictable, and secure manner.

In a further embodiment of the invention, the system is mounted to a ceiling, table, wall, floor, tripod, or cart with locking wheels.

In a further embodiment of the invention, the table is a fluoroscopy table.

In a further embodiment of the invention, the fluoroscopy table has left and right sides providing a first and second support and the system is further secured to the floor of the table with a third support.

In a further embodiment of the invention, the system comprises a circular monorail effective to support one or more robotic devices for remote mapping or ablation with one or more catheters.

In a further embodiment of the invention, the elongated medical device is a pacemaker and/or defibrillator lead.

In a further embodiment of the invention, the robotic device can advance and remove a lead and/or rotate the lead clockwise and counter-clockwise.

In a further embodiment of the invention, the system further comprises means for securing and/or deploying a lead for pacing or shocking, i.e., cardioverting or defibrillation, within the coronary sinus vein or its branches.

In a further embodiment of the invention, a lead capable of applying low and/or high voltage therapy to the left atrium or the left ventricle is deployed.

In a further embodiment of the invention, the medical device is a guide wire or stylet.

In a further embodiment of the invention, the robotic device can advance and remove the guide wire or stylet and/or rotate the guide wire or stylet clockwise or counter-clockwise.

In a further embodiment of the invention, the handle controller comprises:

a handle control assembly configured to receive a control handle of an elongated medical device, the elongated medical device having at least three ranges of motion and a distal end;

a first motor connected to the handle control assembly and effective to at least move the elongated medical device forward and/or backward;

a second motor connected to the handle control assembly and effective to at least rotate the elongated medical device;

a third motor connected to the handle control assembly and effective to at least deflect the distal end in at least a first direction; and a controller unit connected to the first, second and third motors.

In a further embodiment of the invention, the first motor is connected to an externally threaded drive screw; the handle control assembly is connected to an internally threaded drive support; and the drive screw is mated with the drive support.

In a further embodiment of the invention, the handle controller is connected to a linear sled.

In a further embodiment of the invention, the sled member is effective to advance the elongated medical device from the handle controller to a feeder.

In a further embodiment of the invention, the sled member moves along a rail or rails on a sled base.

In a further embodiment of the invention, the sled base is connected to an introducer, the introducer including a clip effective to inhibit buckling of the sheath.

In a further embodiment of the invention, a specially designed clip is capable of securely attaching the end of the handle controller to an introducer sheath to maintain a short fixed distance between the handle controller and the sled base and prevent catheter buckling during remote catheter manipulation.

In a further embodiment of the invention, the medical device is a commercially available steerable catheter, introducer sheath, pacing or defibrillation lead, guide wire, or stylet.

In a further embodiment of the invention, a method for using a remotely controlled catheter insertion device comprises: inserting the control handle of a catheter onto a handle controller coupled to a linear sled; operating the controls of a remote controller; advancing said sled member on a sled base; positioning the sled member relative to the sled base; inserting said catheter into the interior of said sled base, said interior being a sterile environment, advancing said catheter to the end of said sled bed; engaging said catheter with a sterile catheter introducer disposed at the distal end of said sled base, said catheter introducer further engaged with a patient's body; and introducing said catheter into a patient's body.

In a further embodiment of the invention, the handle controller may be manually moved back and forth on the linear sled.

In a further embodiment of the invention, the sled base is covered in a sterile drape, effective to maintain sterility within the system.

In a further embodiment of the invention, the catheter is disposed in a conically shaped lumened catheter feeder effective to secure the catheter to the handle controller.

In a further embodiment of the invention, the handle controller may be removed from the sled base for manual manipulation.

In a further embodiment of the invention, the catheter may be disengaged from the handle controller and then re-engaged while maintaining sterility.

In a further embodiment of the invention, a system for remotely controlling the positioning of an elongated medical device within the body of a patient, comprises:
a robotic device configured to position the medical device within a body of a patient, the robotic device comprising:
   a handle controller effective to manipulate any control on the elongated medical device, which comprises a handle control assembly and a modular plate;
   an elongated medical device coupled to the modular plate;
   a driver effective to move said sled member forward and backward along a rail or rails;
   an introducer effective to deliver the medical device inside the body; and
   a remote controller effective to control the robotic device.

In a further embodiment of the invention, the handle control assembly is modular, each module being adaptable to a particular type of medical device.

In a further embodiment of the invention, the handle control assembly is adaptable to a variety of medical devices.

In a further embodiment of the invention, a method for maintaining the sterility of an elongated medical device prior to insertion into a patient, comprises:
   securing an elongated medical device onto a robotic device, which robotic device moves along a rail system, said rail system having a sterilized chamber disposed within the rail system;
   inserting the elongated medical device into said sterilized chamber of said rail system;
   advancing the elongated medical device to a sterilized catheter introducer, said introducer disposed proximal to a patient's body; and
   inserting said elongated medical device into said patient's body.

In a further embodiment of the invention, a method of introducing a catheter into a patient's body comprises:
   positioning a catheter on a modular plate adapted to accept a catheter;
   attaching said modular plate to a sled member coupled to a handle controller, wherein said handle controller is effective to change the position of said modular plate, wherein said sled is disposed on an elongated sled base having a proximal and distal end, said distal end;
   positioning the catheter within said sled bed, wherein the interior of said sled bed is a sealed sterile environment;
   advancing said catheter coupled to said sled to the distal end of said sled bed, wherein said catheter interacts with an introducer proximal to a patient's body; and
   introducing said catheter into said patient's body.

In a further embodiment of the invention, a method comprises monitoring the position of said catheter within said patient's body remotely and controlling the movement of said catheter using a remote controller.

In a further embodiment of the invention, the remote controller is configured to mimic the handle of a standard catheter.

In a further embodiment of the invention, a mounting assembly for mounting a sled base comprises:
   an elongate plate having a surface adapted for connection to a sled base;
   a connector member connected to said elongate plate structured and arranged for manipulating the position of the elongate plate; a rail for translation of said elongate plate in one dimension; and
   a pair of mounting members for mounting said rail onto a bed structure, the mounting members adapted for connection to lateral rails of said bed structure, wherein said mounting members may be translated in one dimension along said lateral rails.

In a further embodiment of the invention, a system for remotely controlling the positioning of an elongated medical device within the body of a patient, the system comprises:
   a robotic device configured to position the elongated medical device within a body of a patient, the robotic device comprising:
      a handle controller effective to manipulate any control on the medical device, said handle controller comprising a handle control assembly and a modular plate;
      a medical device coupled to the modular plate;
      a sled member coupled to the handle controller;
      a sled base having a rail or rails;
      a driver effective to move said sled member forward and backward along a rail or rails; and
      an introducer effective to deliver the medical device inside the body;
   a remote controller effective to control the robotic device; and
   a mounting assembly for mounting said robotic device comprising:
      an elongate plate having a surface adapted for connection to said robotic device;
      a connector member connected to said elongate plate structured and arranged for manipulating the position of the elongate plate;
      a rail for translation of said elongate plate in one dimension; and
      a pair of mounting members for mounting said rail onto a bed structure, the mounting members adapted for connection to lateral rails of said bed structure, wherein said mounting members may be translated in one dimension along said lateral rails.

In a further embodiment of the invention, a system for remotely controlling the positioning of two or more medical devices within the body of a patient, comprises:
   two or more robotic devices each configured to position an elongated medical device within a body of a patient, each robotic device comprising: a handle controller effective to manipulate any control on the medical device;
   a sled member coupled to the handle controller;
   a sled base having a rail or rails;
   a driver effective to move said sled member forward and backward along the rail or rails; and an introducer effective to deliver the medical device inside the body;
   a remote controller effective to control each robotic device; and
   a mounting assembly for mounting each said robotic device comprising:
      an elongated plate having a surface adapted for connection to each said robotic device;
      a connector member connected to said elongate plate structured and arranged for manipulating the position of the elongate plate;

a rail for translation of said elongate plate in one dimension; and a pair of mounting members for mounting said rail onto a bed structure, the mounting members adapted for connection to lateral rails of said bed structure, wherein said mounting members may be translated in one dimension along said lateral rails.

In a further embodiment of the invention, a system for remotely controlling the positioning within the body of a patient of an elongated medical device having a proximal end, comprises: a robotic device configured to position the medical device within the body of the patient; and a remote controller configured to control the robotic device, wherein the robotic device comprises a handle controller to receive the proximal end of the medical device.

In a further embodiment of the invention, a mounting assembly is provided for mounting a sled base. The mounting assembly comprises an elongate plate having a surface adapted for connection to a sled base, a connector member connected to said elongate plate structured and arranged for manipulating the position of the elongate plate; a rail for translation of said elongate plate in one dimension; and a pair of mounting members for mounting said rail onto a bed structure, the mounting members adapted for connection to lateral rails of said bed structure, wherein said mounting members may be translated in one dimension along said lateral rails.

BRIEF DESCRIPTION OF THE DRAWINGS

The following drawings, which are included herewith and form a part of this application, are intended to be illustrative and not limiting of the scope of the present invention.

DETAILED DESCRIPTION OF THE INVENTION

Figure 1:
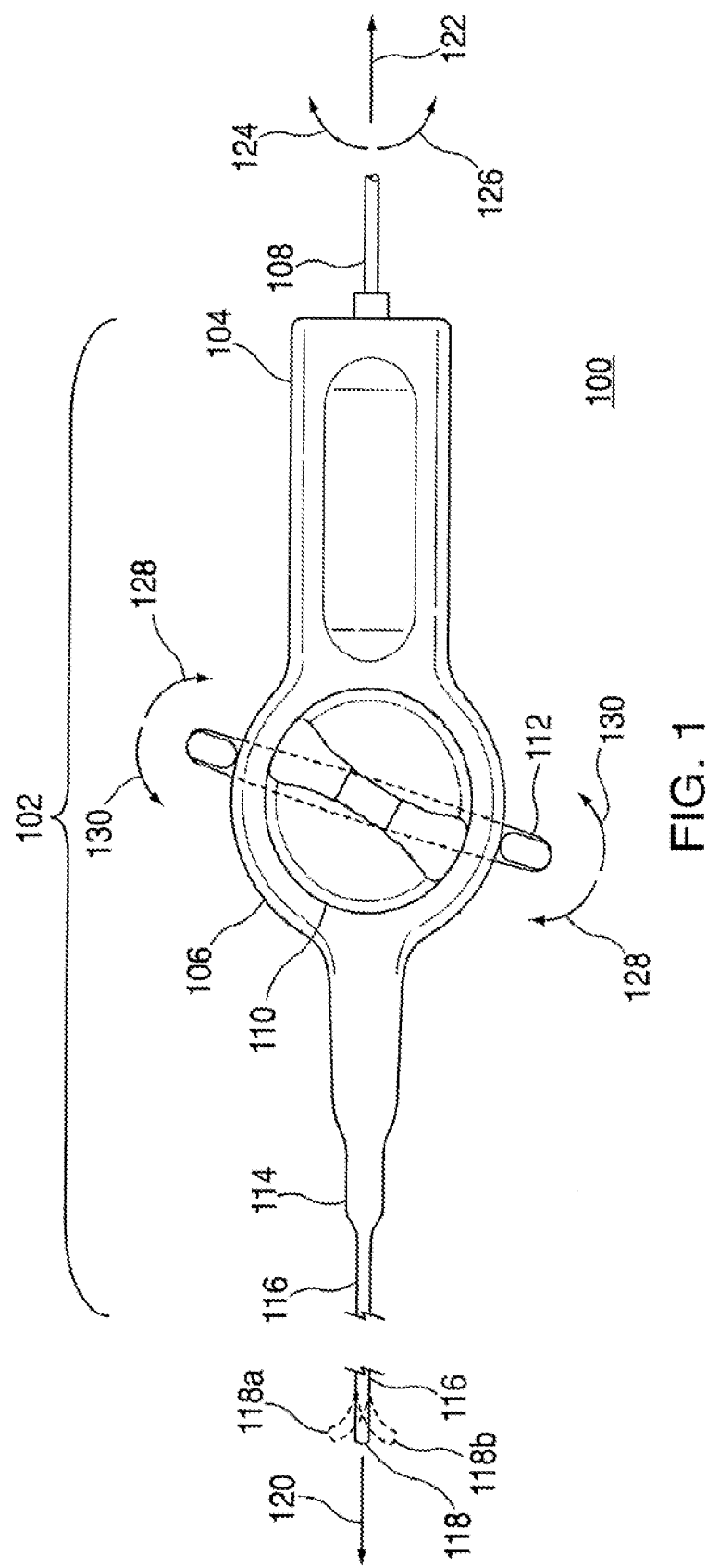
FIG. 1 is a top view of a catheter which could be used in accordance with an embodiment of the invention.

The invention can perhaps be better appreciated by making reference to the drawings. In FIG. 1, a catheter 100 is shown in schematic fashion. Catheter 100 comprises a handle portion 102 which may be gripped by a user. Handle portion 102 comprises a proximal end 104 and a grip portion 106. Inserted into proximal end 104 may be wires 108 or tubing which could provide electricity, coolant, heat, etc., to catheter 100. Grip 106 comprises an adjustment dial 110 which may be used to adjust the tension of a knob 112. Handle 102 terminates in a distal flexible end portion 114 which in turn is in communication with a distally extending catheter sheath or tubular member 116.

As it is known in the art, catheter sheath 116 may be inserted into a patient by use of various known procedures and devices. Catheter sheath 116 terminates in a distal end 118. Distal end 118 may include, for example, electrodes for supplying electrical stimulation, coolant, heat, etc.

Catheter sheath 116 is physically attached to handle 102 so that movement of handle 102 forward or backward in the direction of arrow 120 or 122 causes catheter sheath 116, as well as distal end 118, to move similarly. Rotation or torquing of handle 102 in a clockwise or counterclockwise manner as is shown by arrows 124 and 126, will impart a similar rotation to catheter sheath 116. Rotation of knob 112 in the direction of arrow 128 or 130 causes deflection of distal end 118 in one of the directions shown as 118a and 118b. Thus, when used manually, commercially available catheters can operate in six ranges of motion: forward and backward in the direction of arrows 120 and 122, rotation in the direction of arrows 124 and 126, and deflection to positions such as 118a and 118b. Known remote control catheter insertion devices are not capable of utilizing all of these ranges as embodiments herein can.

The embodiment shown in the drawings primarily relates to the application of the invention to a steerable catheter. However, the robotic control system of the invention is also applicable to other flexible medical devices such as guide wires, introducer sheaths, guiding catheters, or any similar elongated medical device.

Figure 2:
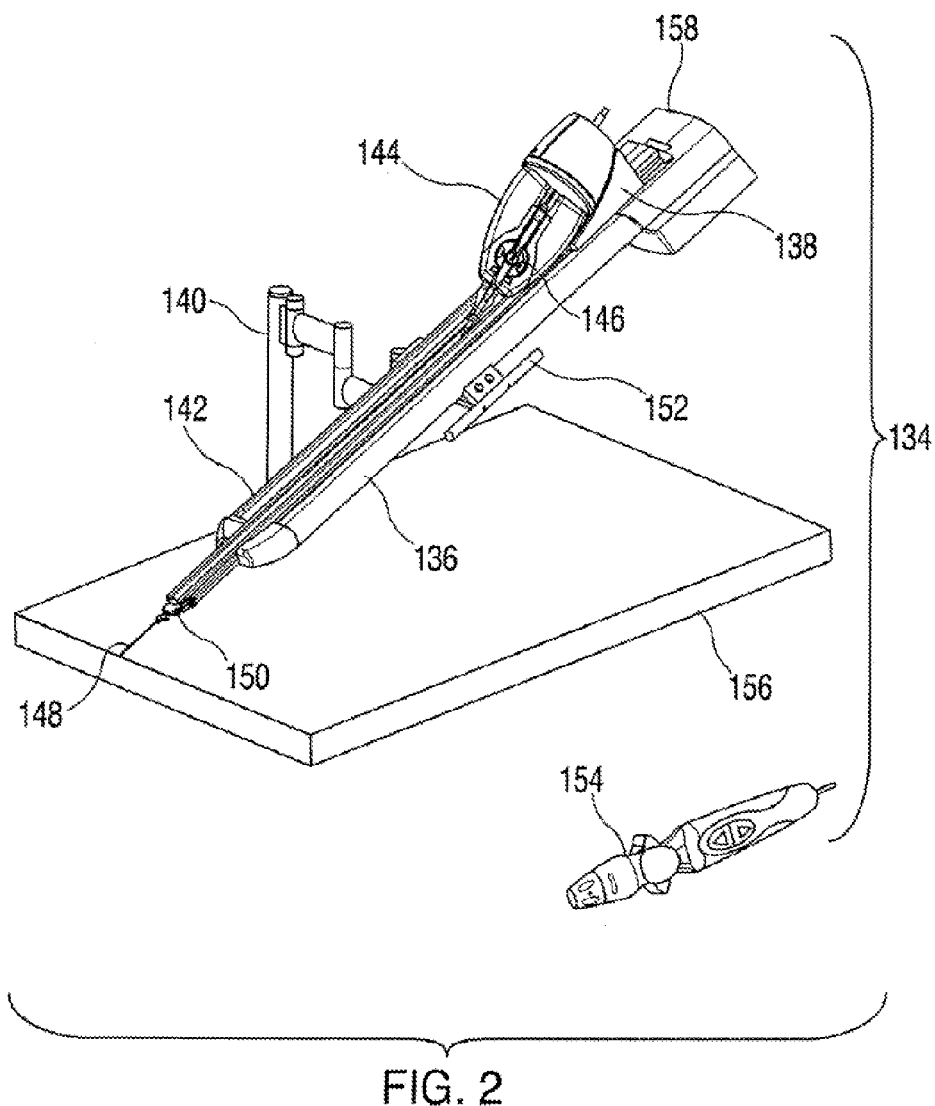
FIG. 2 is an oblique view of a remotely controlled catheter insertion system in accordance with another embodiment of the invention.
Figure 3:
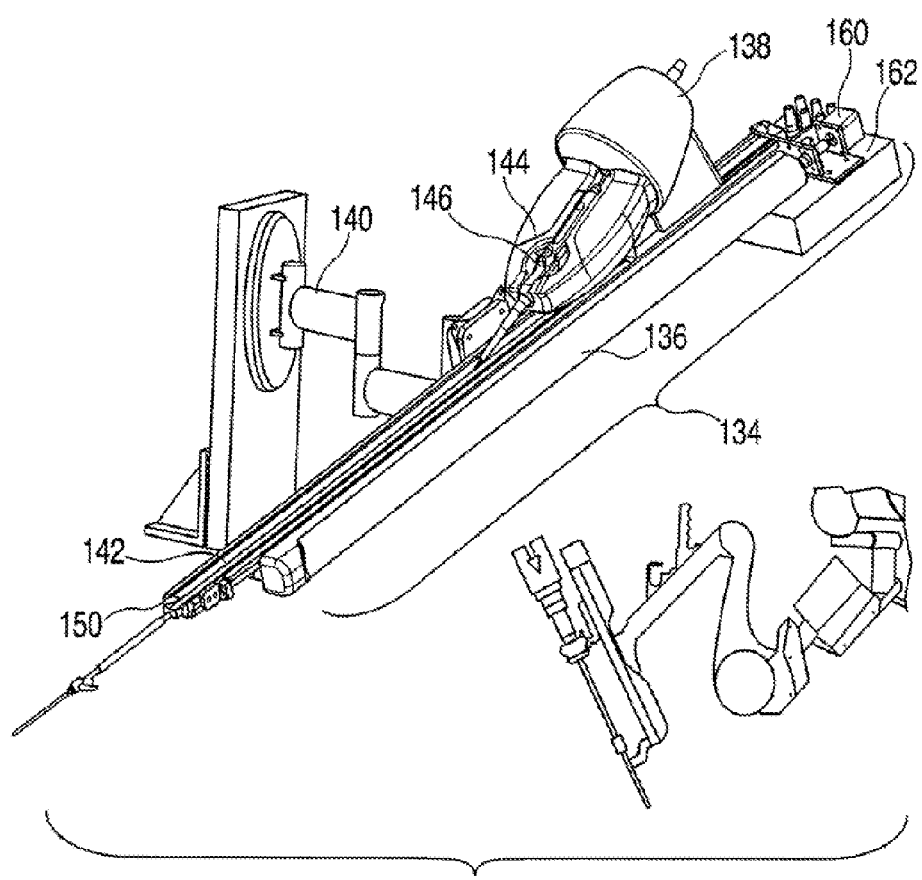
FIG. 3 is an oblique view of a remotely controlled catheter insertion system in accordance with another embodiment of the invention.

FIGS. 2 and 3 illustrate a remotely controlled catheter insertion system 134 in accordance with an embodiment of the invention. System 134 includes a linear sled bed or base 136 which supports a linear sled member 138, a mounting arm 140 which supports sled base 136, a sterile guide barrier 142, a handle controller 144, a catheter dock or handle control assembly 146, a catheter introducer 148, and a catheter introducer coupling 150. In an embodiment, sled base 136 may be positioned using a local control and positioning handle 152 or a remote controller 154. Mounting arm 140 connects to sled base 136 and allows for vertical (downward and upward) rotational motion and horizontal (left and right) rotational motion. Mounting arm 140 may be moved manually or mechanically through the use of a remote control. Mounting arm 140 may be attached to either the left or right side bars of an operative surface 156 such as a fluoroscopy table and may optionally be further attached to the foot of the table with a third support in a tripod-like configuration.

Alternatively, a circular monorail or other configuration of rails may support one or more robots for the purpose of remote mapping and ablation or one or more catheters.

With reference again to FIGS. 2 and 3, motor housing 158 houses a motor 160 mounted on a support surface 162. Motor 160 receives power and signal control through the use of wires fed through a wire housing (not shown) and terminal connectors (not shown). As discussed in more detail below, wires supply both power and signal control to motor 160 and handle controller 144. Motor 160 rotates a drive screw 164 to advance sled member 138. Motor 160 easily moves handle controller 144 and sled member 138 back and forth on sled base 136 to help with catheter placement.

Figure 8:
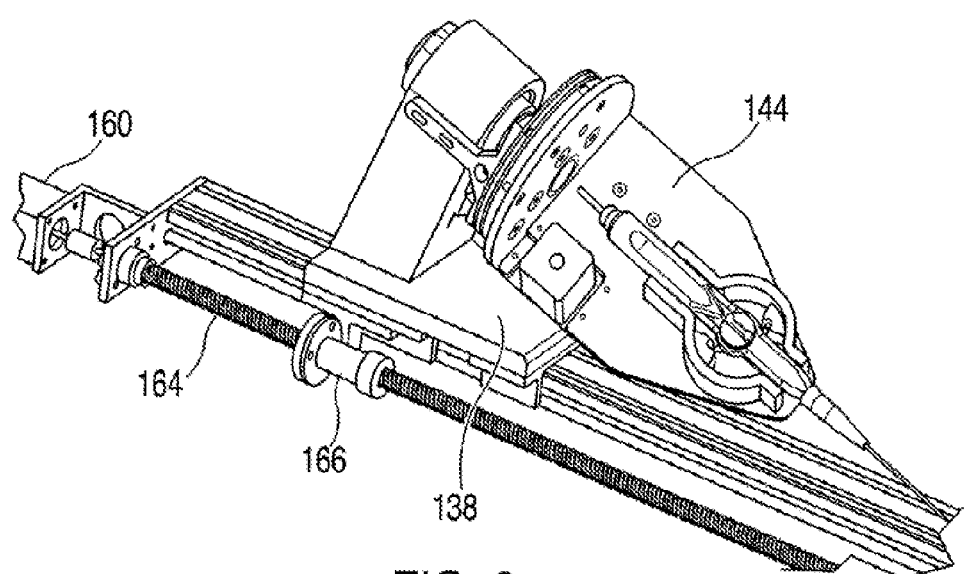
FIG. 8 is a lateral perspective view of the drive screw and sled member in accordance with an embodiment of the invention.
Figure 8A:
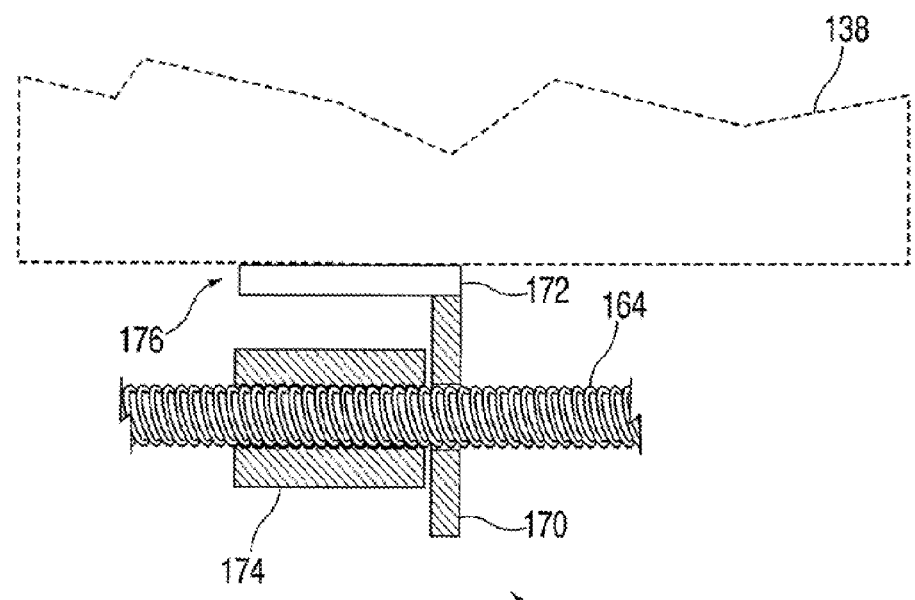
FIG. 8A is a cutaway view of the drive screw in accordance with an embodiment of the invention.

Handle controller 144 is coupled to sled member 138. With reference to FIGS. 8 and 8a, sled member 138 with handle controller 144 is operatively connected to a drive screw 164 through a drive support 166. Drive support 166 is internally threaded, and the internal threads of drive support 166 engage with the external threads of drive screw 164. In this way, when drive screw 164 rotates, drive support 166 moves forward or backward due to engagement of internal threads in drive support 166 and the external threads of drive screw 164. Drive screw 164 may be disposed inside sled base 136. The distal and proximal ends of sled base 136 limit the movement of drive support 166 and thereby, in turn, limit the movement of handle controller 144 and sled member 138.

As shown more clearly in FIG. 8A, drive support 166 includes a support base 170 attached to a cantilevered top support 172 and attached to an internally threaded member 174. Top support 172 is attached to a support base 176 of sled member 138, as shown in dotted lines. Drive screw 164 is fed through a hole in support base 170 and mates with threads of internally threaded member 174 to move backward or forward. Such movement is imparted to support base 170 to top support 172, and then, in turn, to sled member 138 (and handle controller 144). A sensor may be disposed proximate to motor 160, drive screw 164, drive support 166, or sled member 138 to sense movement of sled member 138 and handle controller 144.

Figure 4:
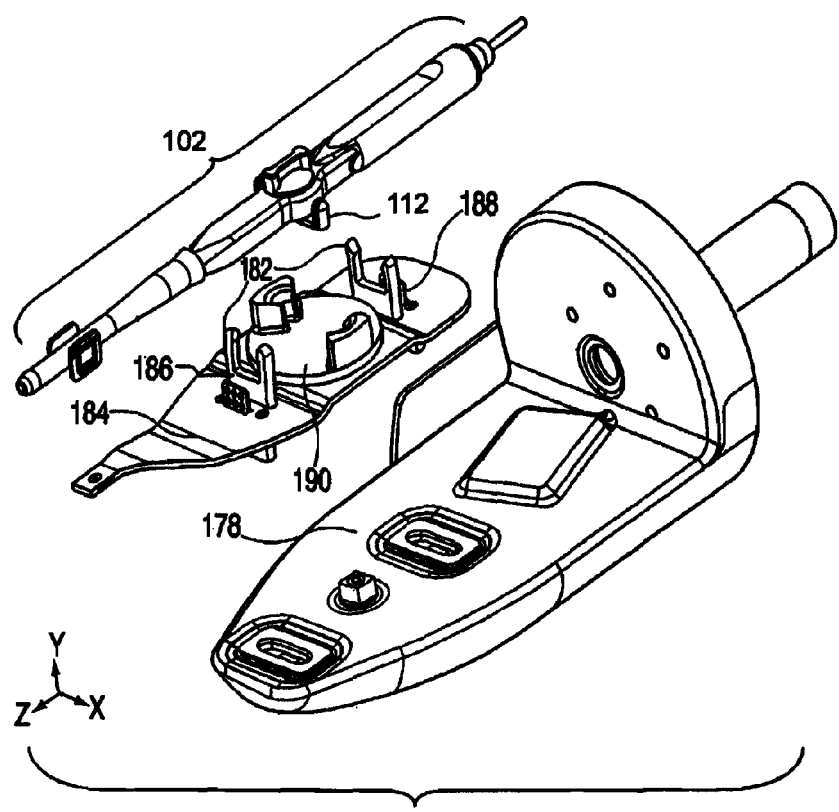
FIG. 4 is a detailed, exploded view of some of the components of a robotic device of the invention.
Figure 5:
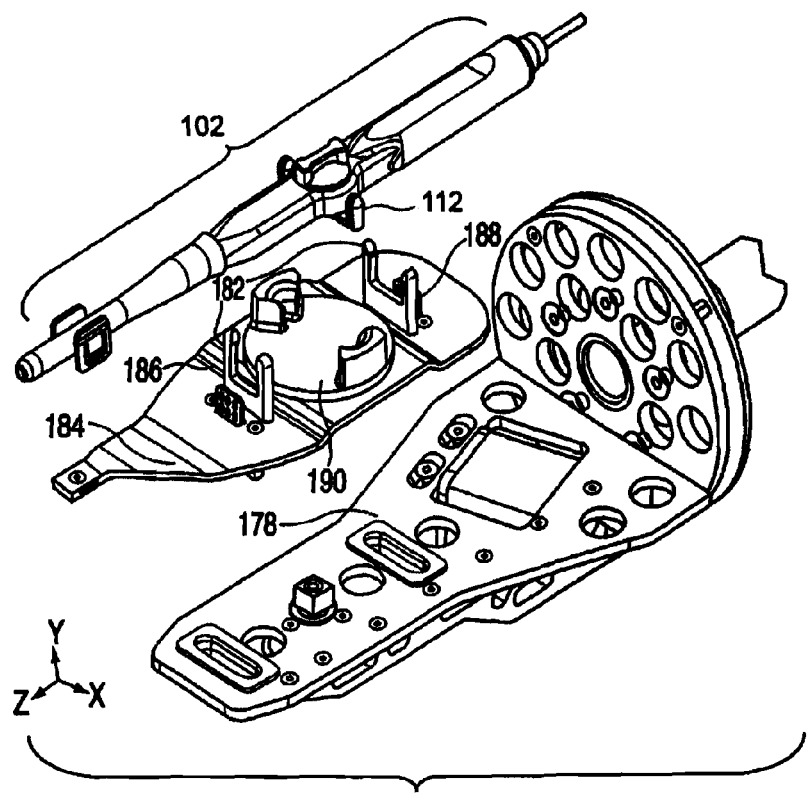
FIG. 5 is a detailed, exploded view of some of the components of a robotic device of the invention.
Figure 6:
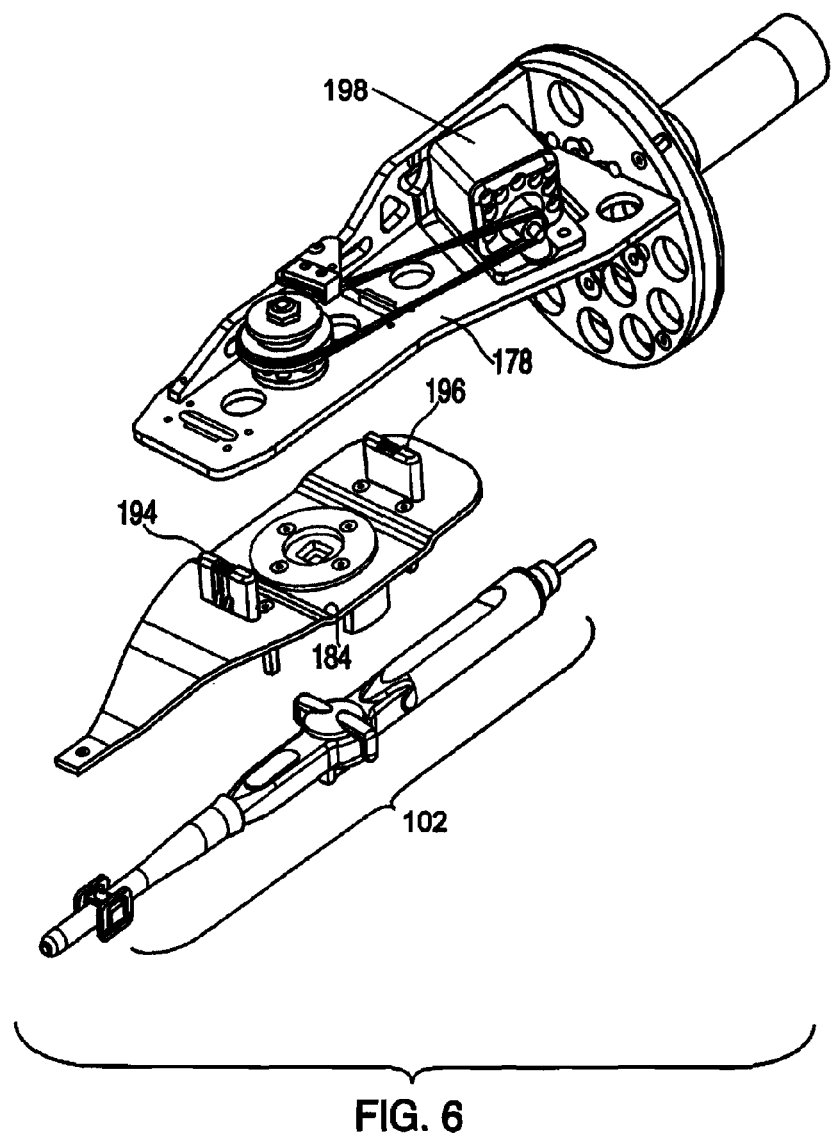
FIG. 6 is an underside, detailed view of some of the components of a robotic device of the invention.

The system as described in FIGS. 4, 5, and 6 depicts a sled member 178, in which a catheter control handle is received in a handle control assembly 182 and mounted to a modular plate 184. Handle control assembly 182 comprises clamps 186 and 188 and molded nest 190. The knob 112 of catheter handle 102 is secured in molded nest 190 by friction or snap-in fit.

Sled member 178 is attached to the catheter handle 102 by modular plate 184 and handle control assembly 182. Modular plate 184 and handle control assembly 182 are specific to the type/manufacture of the catheter 100 to be used with the invention. Different modular plates 184 and handle control assemblies 182 may be used dependent upon the type/make of catheter used. The modular plates 184 and handle control assemblies 182 may be sterilizable, disposable, or both.

It is a significant feature of the invention that commercially available, off the shelf catheters can be used. As modular plate 184 is detachable from sled member 178, different handles may be used for different types of catheters 100. In the example shown in FIG. 1, a BLAZER II XP™ cardiac ablation catheter (available from Boston Scientific Corporation, Natick, Mass.) with a corresponding modular plate 184 is being used. Other handles and catheters could be used. For example, a SAFIRE™ bi-directional ablation catheter (available from St. Jude Medical, St. Paul, Minn.) may be used along with a corresponding modular plate 184. Similarly, an RF MARINR®, RF CONTRACTR®, or RF CONDUCTR® ablation catheter (available from Medtronic, Inc., Minneapolis, Minn.), might also be used. A fastening mechanism comprising clamps such as clamps 186 and 188 may attach catheter 100 to modular plate 184.

Figure 7:
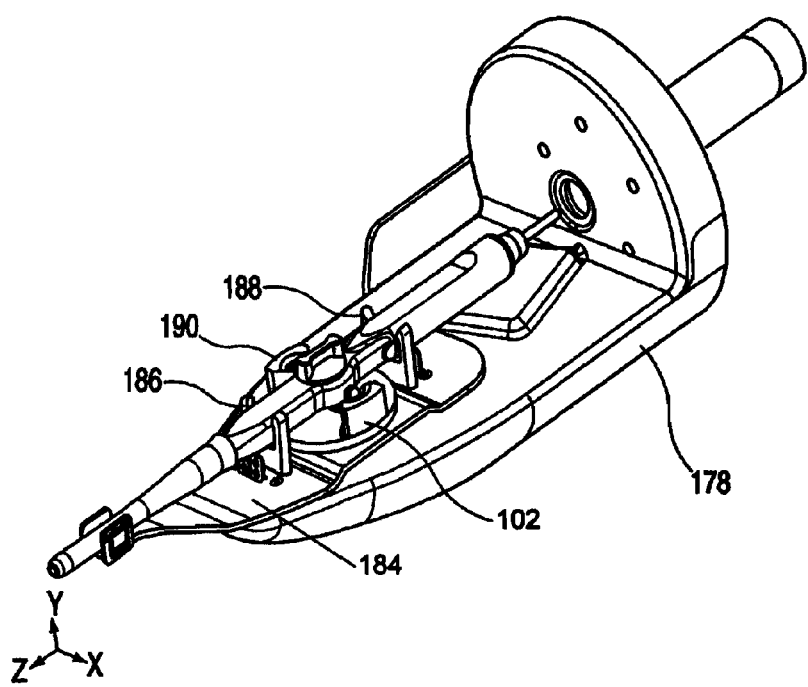
FIG. 7 is a top view of a sled member coupled to a catheter.

With reference to FIGS. 4, 5, and 6, the handle of catheter 100 is engaged into modular plate 184 at three points, namely, clamps 186 and 188 and molded nest 190. The catheter handle 102 may be snap fit into molded nest 190 or secured by friction. The proximal end of catheter handle 102 is mounted to modular plate 184 through the use of clamp 186 and distal end is mounted onto modular plate 184 through the use of clamp 188. In one embodiment, the clamps may be snap fit. If catheter 100 has an additional range of motion, such as the point of deflection in a Medtronic ablation catheter, an additional motor 198 can be attached to move the corresponding control on the handle. Modular plate 184 may subsequently be attached to sled member 178 by snap fit. As seen in FIG. 6, modular plate 184 has protrusions 194 and 196 effective to secure modular plate 184 to sled member 178. FIG. 7 illustrates modular plate 184, attached to sled member 178 and the catheter handle 102.

In an embodiment, sled member 178 may be equipped with rear and/or front end force sensors (not shown) to gauge force in three zones. A display may be located on modular plate 184, the remote control station 290, or elsewhere. In an embodiment, the display may indicate forces of low, medium, and high. These indications may be represented by colored lights, including green, yellow, and red respectively, or bars of light, such as one bar, two bar, or three bars. In a further embodiment, the display may further include an audio sensor which emits a noise when the incorrect amount of force is applied.

Figure 9:
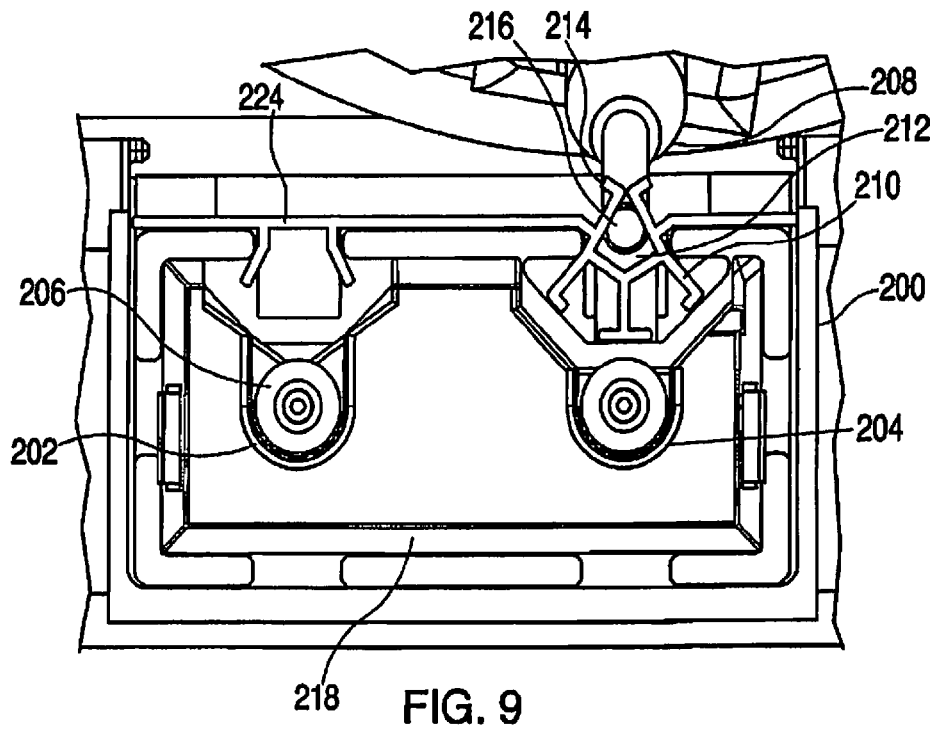
FIG. 9 is a front view of the inner nose cone of the sled member bed in accordance with an embodiment of the invention, wherein a catheter feeder and wipers may be seen.
Figure 9A:
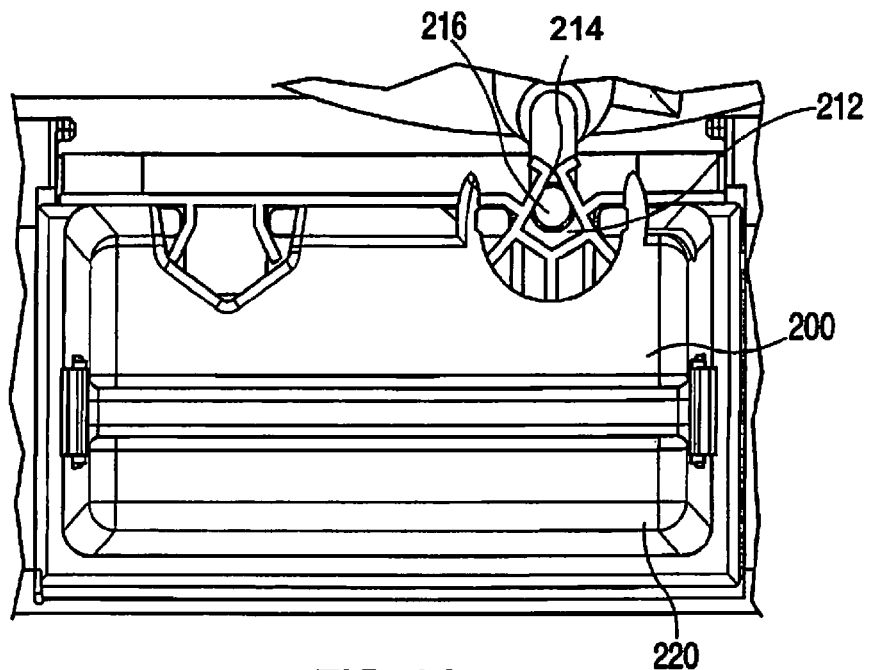
FIG. 9A is a front view of the outer nose cone of the sled member bed in accordance with an embodiment of the invention.
Figure 10:
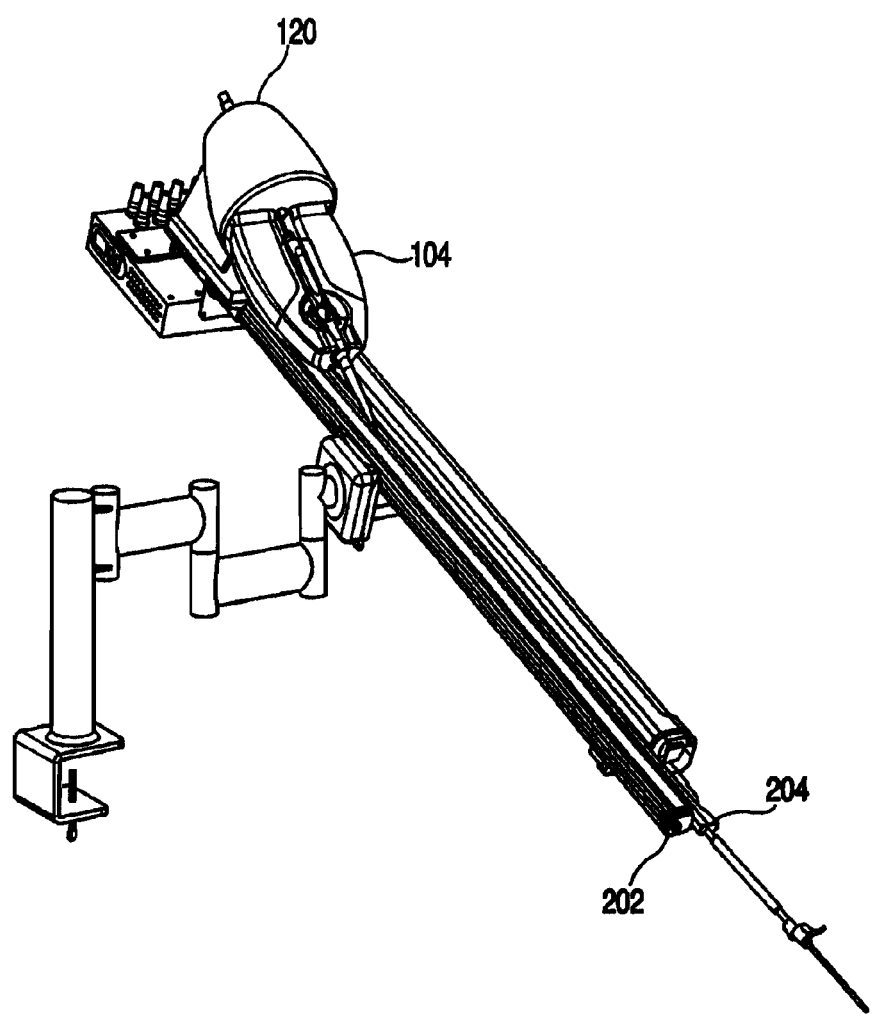
FIG. 10 is a top perspective view with a cutaway of a system of the invention attached to a mounting arm accordance with an embodiment of the invention.

With reference to FIGS. 9, 9A, and 10, linear sled base 200 comprises two rails 202 and 204, which run parallel to each other and to the edges of sled base 200. In one embodiment, drive screw 206 may be located in rail 202 or rail 204 and run the length of the rail. Sled member 208 is located above recess 204 and is adapted to advance along the rail. A slotted flexible extrusion 210 may be disposed in rail 204. Slotted flexible extrusion 210 contains a recess 212 adapted to accept a catheter. The opening to recess 212 comprises dual flexible liners 214, which come together to form a delivery channel or lumen in which catheter 100 glides as it is inserted into the patient. Slotted flexible extrusion 210 may run the length of sled base 200. As illustrated, proximal end of catheter 100 moves through the sterile rail 204 through the dual flexible liners 214 in the slotted flexible extrusion 210, which is also sterile.

Figure 13:
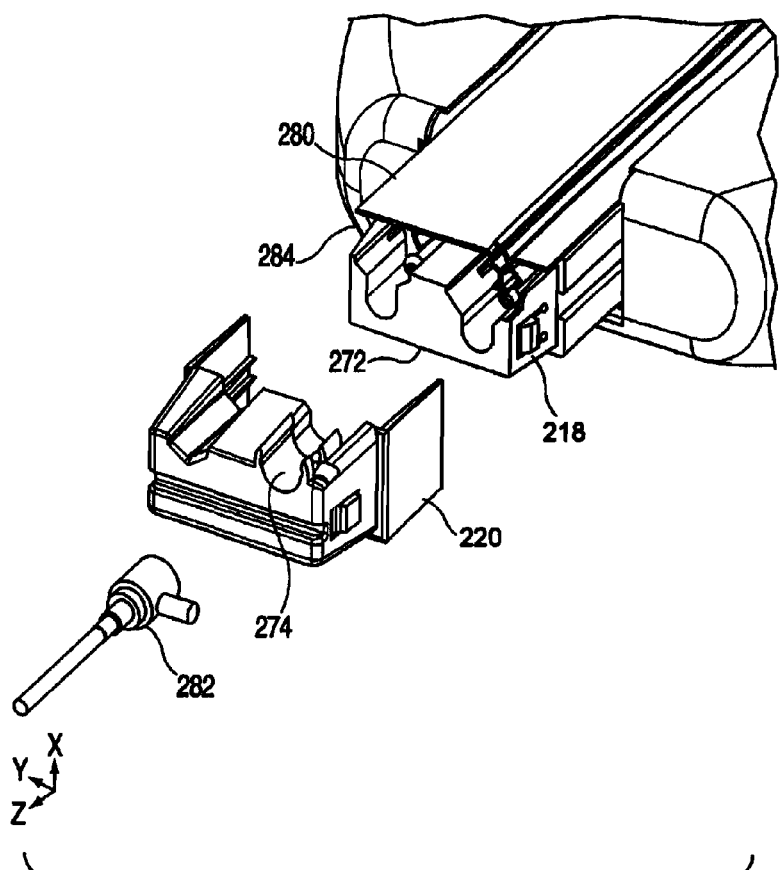
FIG. 13 is a view of a the inner nose cone, outer nose cone and introducer in accordance with an embodiment of the invention.

With reference to FIGS. 9, 9A, and 13, an inner nose cone 218 is attached to the distal end of sled base 200. Inner nose cone 218 may be sterilized prior to use and disposed of after use. Inner nose cone 218 is adapted to accept outer nose cone 220. Outer nose cone 220 covers inner nose cone 218 and the main rail to keep the main rail and inner nose cone 218 behind a sterile field. Latch release features may be built into the outer nose cone 220, which allows a user to disconnect outer nose cone 220 without touching inner nose cone 218. A catheter introducer clamp 274 is incorporated into outer nose cone 220, which eliminates the need to affix catheter introducer clamp 274 to sterile barrier 224. Introducer 282 may be attached by friction or snap fit to introducer clamp 274.

In one embodiment, a sterile barrier 224 may be removably placed on sled base 200 to completely seal sled base 200. Sterile barrier 224 has dual flexible liners 214 (see FIGS. 9 and 9A) located above rail 204 to provide an entry for catheter 216 to be pressed onto and fed into the recess.

Figure 11:
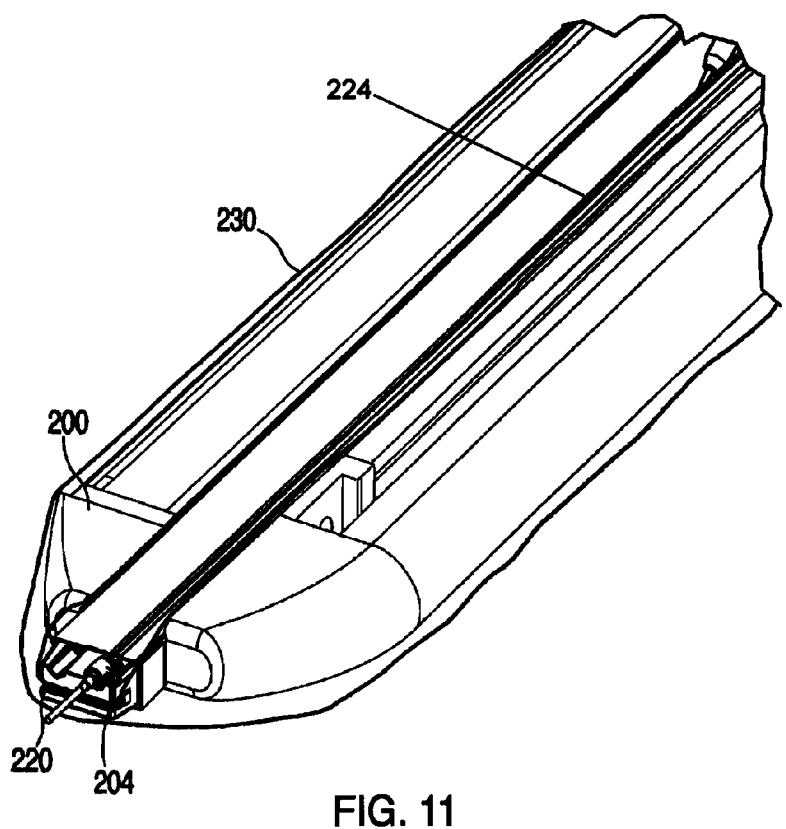
FIG. 11 is a detailed view of the invention with a sterile drape in accordance with an embodiment of the invention.

With reference to FIG. 11, a sterile poly bag 230 may be further used to maintain the sterility of sled base 200. Sterile poly bag 230 has an elastic band that stretches along the length of sterile barrier 224 to allow sled member 208 to slide along rail 204 without binding to sterile poly bag 230. In one embodiment, sterile poly bag 230 covers the entirety of sled base 200 and acts as a barrier between the patient and the device.

Figure 12:
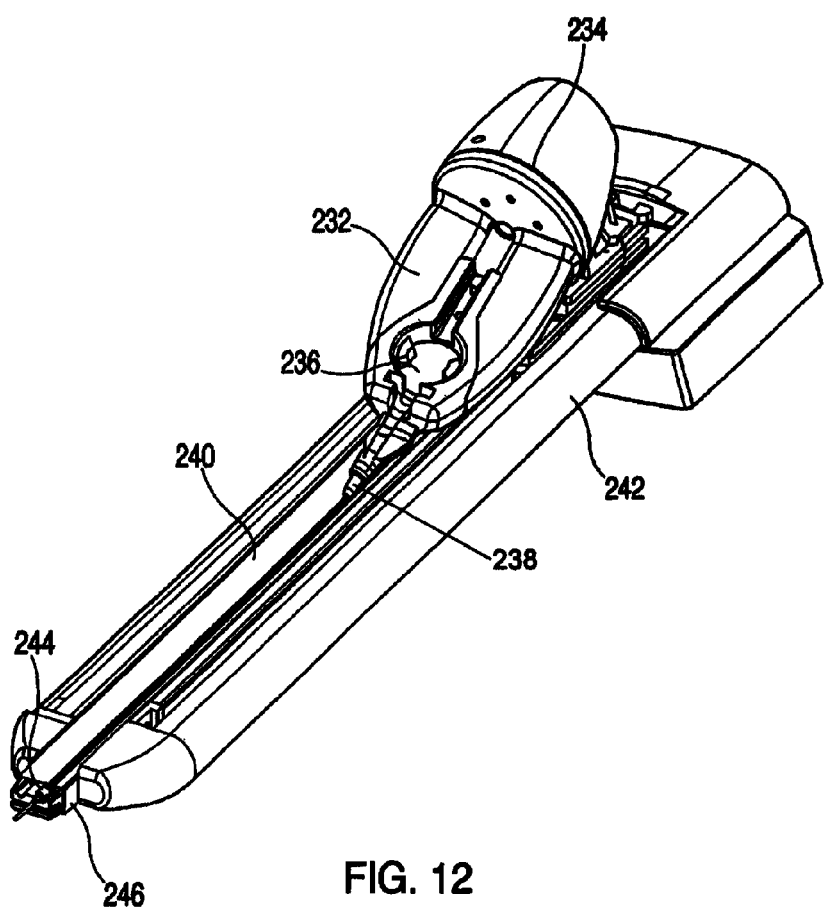
FIG. 12 is a top perspective view of a remotely controlled catheter insertion device in accordance with an embodiment of the invention.

With reference to FIG. 12, in one embodiment, a sterile drape is configured to maintain sterility and permit sterile placement of a catheter in the handle controller 232 and sled member 234 over a sterile field and further permits sterile removal of a catheter for manual manipulations. In one embodiment, the entire system is sterile. The handle of a catheter (not shown) can be received in a molded nest 236. A catheter feeder 238 would direct the distal portion of the catheter through a sterile barrier 240 through a sled base 242 and then through an introducer 244 in nose cone 246.

With reference again to FIG. 1, catheter sheath 116 is very flexible. Such flexibility means that if too much force is applied to catheter sheath 116, catheter sheath 116 may buckle instead of moving forward into a patient. Embodiments of the invention may have various mechanical devices to avoid such buckling. With reference again to FIG. 12, after a flexible catheter sheath is attached to sled member 234, the catheter sheath is inserted through sterile barrier 240 into a rail in sled base 242.

Figure 20:
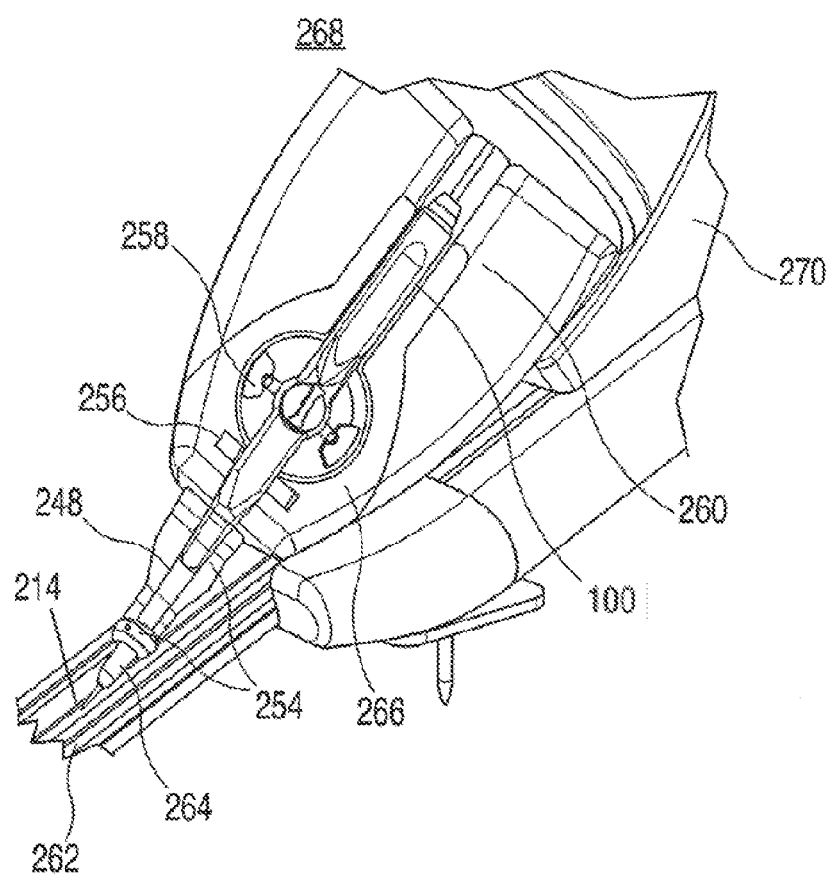
FIG. 20 is a top perspective view of the catheter and feeder of the invention being inserted into the sterile barrier in accordance with an embodiment of the invention.

With reference to FIG. 20, a feeder 248 is attached to the end of a catheter 100. Feeder 248 is supported by feeder support 254 and is attached to catheter 100 by a clasp 256. In one embodiment, feeder 248 is sterile and conically lumened. Feeder 248 may be disposable or resterilizable. Feeder 248, in one embodiment, is 2-4 inches in length and slides up catheter 100 to help to secure the end of catheter 100 to handle controller 260. Feeder 248 further helps to guide catheter 100 into the channel/lumen of slotted flexible extrusion 262 and dual flexible liners 214. Feeder 248 allows robotic manipulation followed by the ability to maintain sterility and remove catheter 100 and perform manual manipulations. In an embodiment, this may be known as a manual over-ride feature. Feeder 248 further permits the ability to return catheter 100 back into the delivery channel by snapping of feeder 248 into modular plate 266 and handle controller assembly 268.

Sled member 270 may be remotely controlled to angle modular plate 266 down towards the rail. Catheter 100 coupled to feeder 248 is further inserted into slotted flexible extrusion 262 in a rail. As handle controller 260 and sled member 270 move forward and backward in direction, catheter 100 moves inside the rail. The catheter may be guided forward and backward along the rail.

To further assist in the feeding of a catheter or sheath and to avoid buckling of the same, a catheter introducer clamp is used. Referring to FIG. 13, rail 272 terminates at catheter introducer clamp 274 and includes an outer nose cone 220 and inner nose cone 218. As discussed previously, a catheter sheath is inserted internally through sterile barrier 280 to rail 272. A catheter introducer 282 maintains a fixed and precise distance (i.e., close proximity) to the catheter or sheath and provides further protection against buckling. The catheter or sheath exits catheter introducer 282.

With reference again to FIG. 1, as discussed, catheter 100 is capable of being manipulated in six ranges of motion: forward and backward 120 and 122, rotation clockwise and counter-clockwise 124 and 126, and deflection of a distal tip to positions 118a and 118b. In system with catheter 100, the movement forward and backward 120 and 122 is controlled through the use of motor 160 and the engagement of drive screw 166 with drive support 164—as can be seen most clearly in FIGS. 8 and 8a. Clockwise and counter-clockwise rotation 124 and 126 is effectuated through the use of the motor imparting motion. The deflection of distal end 118 towards positions 118a and 118b is effectuated through the use of motor 160.

The remote controller 154 of FIG. 2 may be connected by wire or wirelessly to the system of the invention. Controller 154 may have a button for a dual robotic system scenario in which the same handle controller could operate two different robotic systems by using a switch to switch the signals back and forth. In addition, the controller may have sensors, such as infrared or temperature, so that it will not operate unless a human is holding it, a variation on the "dead man's switch" concept.

The wireless remote controller should be of a size and shape to be comfortable in an operator's hand, preferably the size and shape of a handle of a standard steerable elongated medical device.

Figure 14:
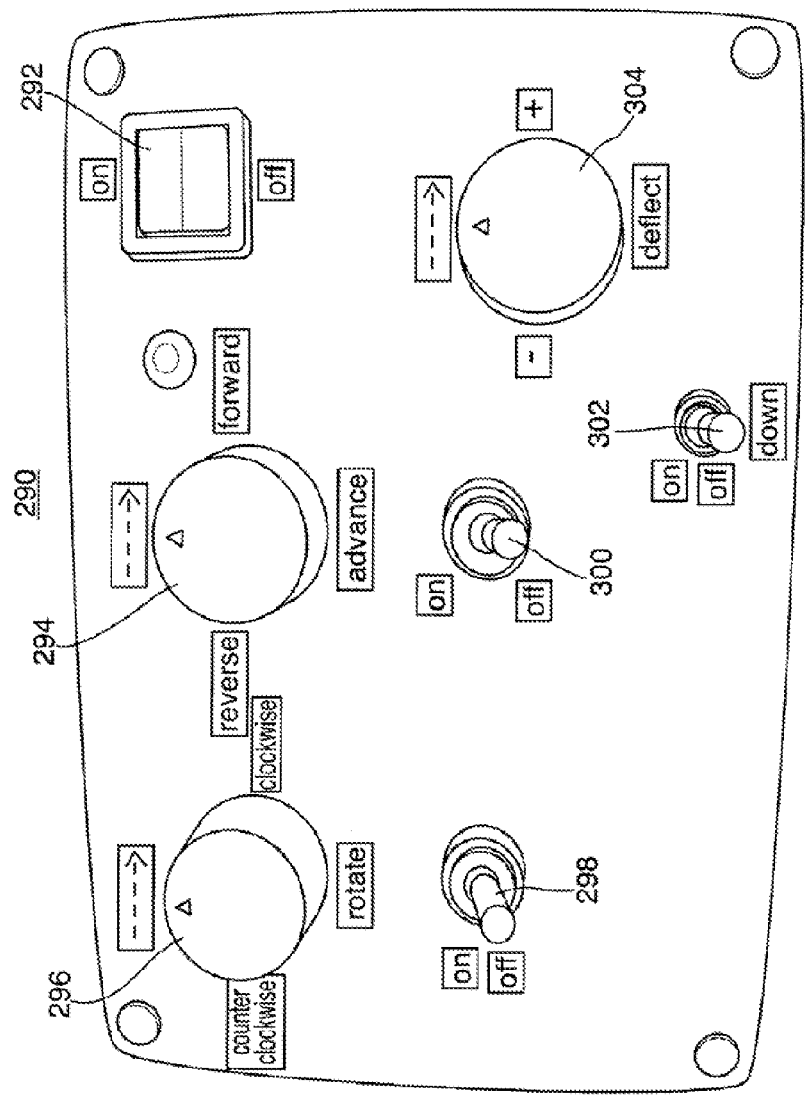
FIG. 14 is a top view of a controller in accordance with an embodiment of the invention.

With reference to FIG. 14, there is shown a remote control station 290 which could be used in accordance with an embodiment of the invention. Remote control station 290 has a master switch 292 effective to supply power to each of the motors connected to remote control station 290. A forward/reverse dial 294 is connected to a motor so that movement of dial 294 supplies power and a control signal to a motor and imparts forward and backward movement of a catheter. A forward/reverse power switch 300 selectively supplies power to dial 294. A rotation dial 296 is connected to a motor so that movement of dial 296 supplies power and a control signal to the motor and causes rotational movement of a catheter. A rotation power switch 298 selectively supplies power to dial 296. A deflection dial 304 is connected to a motor (see FIG. 8). Movement of dial 294 supplies power and control signals to motor 160 and imparts deflection of the distal end of a catheter. A deflection power switch 302 selectively supplies power to dial 304. In this way, all of the ranges of movement of the catheter can be controlled through the use of remote control 290. If the catheter has wires attached to it for electricity, heating or cooling such wires may also be connected to control station 290. Dials may be used to generate on/off signals or analog signals corresponding to various speeds for the motors.

Figure 15:
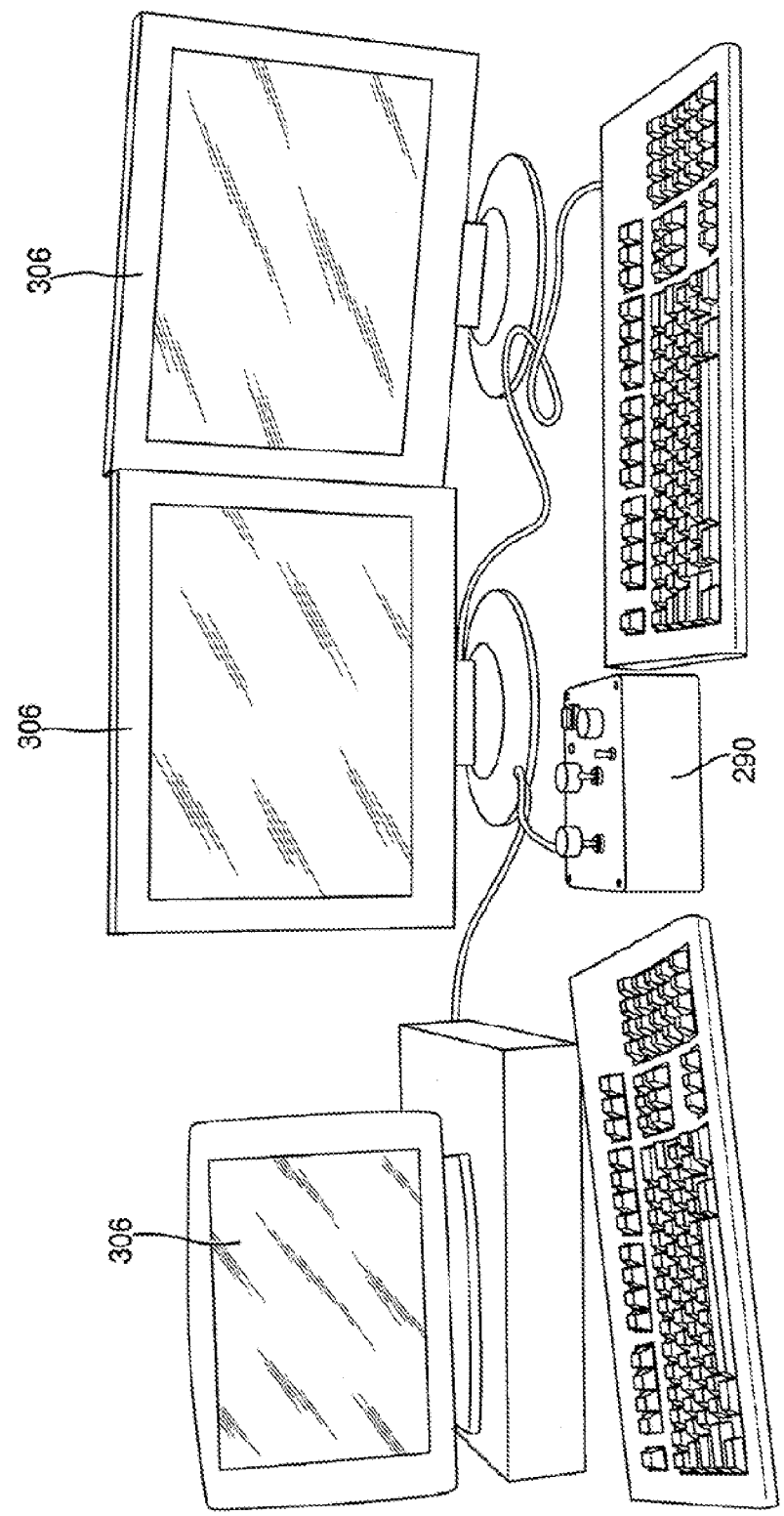
FIG. 15 is a front view of a system layout in accordance with an embodiment of the invention.

With reference now to FIG. 15, remote control station 290 can be disposed at a location which is spaced from the rest of the system of the invention. For example, a technician or doctor operating the system may control a catheter remotely through the use of remote control station 290. Remote control station 290 may even be in a separate room from the rest of the system. A technician may be able to view screens 306 supplying information regarding a procedure (such as fluoroscopy) while operating control station 290. Control station 290 can be connected to the system of the invention in a variety of means including wires and/or wireless connections. It is within the scope of the invention that the system described herein may be operated simultaneously or in conjunction with other mapping and/or visualization systems. Such other systems include a CARTO® (available from Biosense Webster, Inc., Diamond Bar, Calif.) or EnSite™ (available from Endocardial Solutions Inc., St. Paul, Minn.) mapping system or conventional infrared or ultrasound visualization systems.

Remote control station 290 may be configured to be similar in look, feel, design and manipulation to the handle of a standard catheter. Remote control station 290 may permit catheter advancement/withdrawal together with deflection with one hand and rotation with the other hand via use of a knob. On the other hand, one could have advancement/withdrawal with one hand and rotation of knob and deflection with the other.

Figure 16:
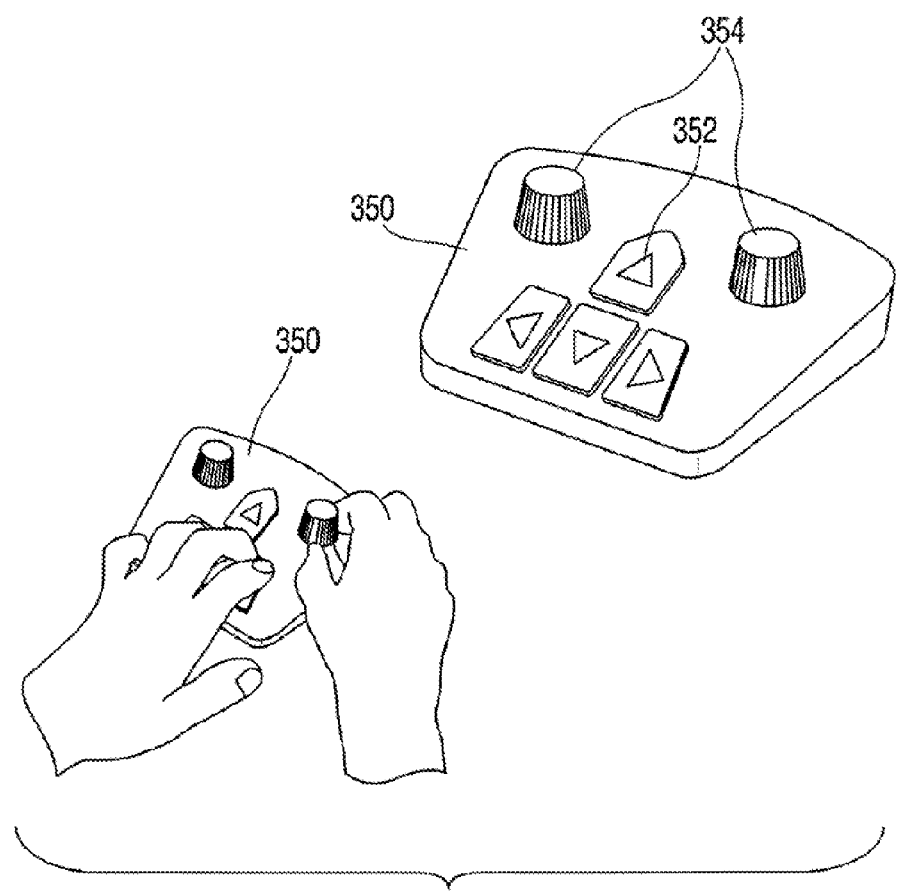
FIG. 16 is a top perspective view of a remote controller in accordance with an embodiment of the invention.

In one embodiment, a remote control 350, as seen in FIG. 16 may have directional functions such as up/down and in/out or left/right, or left roll/right roll which may be controlled by buttons 352. Dials 354 may control left and right articulation. In this embodiment, it takes two hands to control the remote control.

Figure 17:
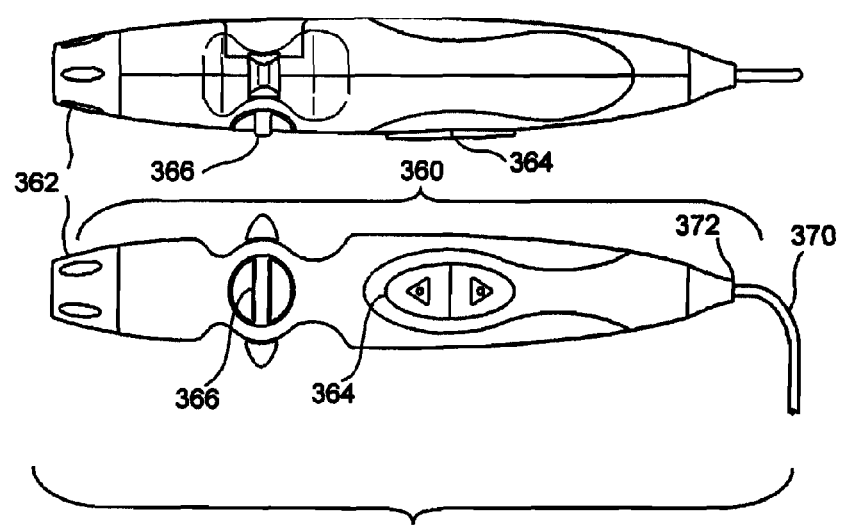
FIG. 17 is a top view of a remote controller in accordance with an embodiment of the invention.
Figure 18:
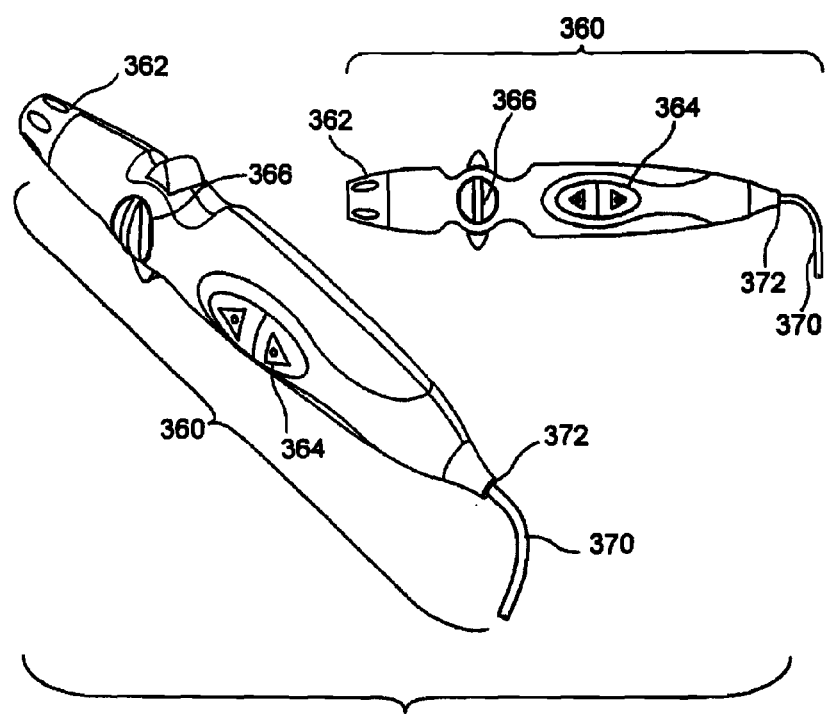
FIG. 18 is a top perspective view of a remote controller in accordance with an embodiment of the invention.

FIGS. 17 and 18 depict a second embodiment of a remote controller of the invention. Remote controller 360 imitates the look and feel of a standard catheter for ease in controls. Remote controller 360 is designed for use with a single hand. Distal end 362 may be rotated to control right roll and left roll of a catheter such as catheter 100. Buttons 364 located on the body of remote controller 360 control in and out functionalities. At the indentation close to the distal end 362 of remote controller 360, knob 366 may be used to control deflection or other articulation. Wire 370 located at proximal end 372 connects remote controller 360 to a power source.

Figure 19:
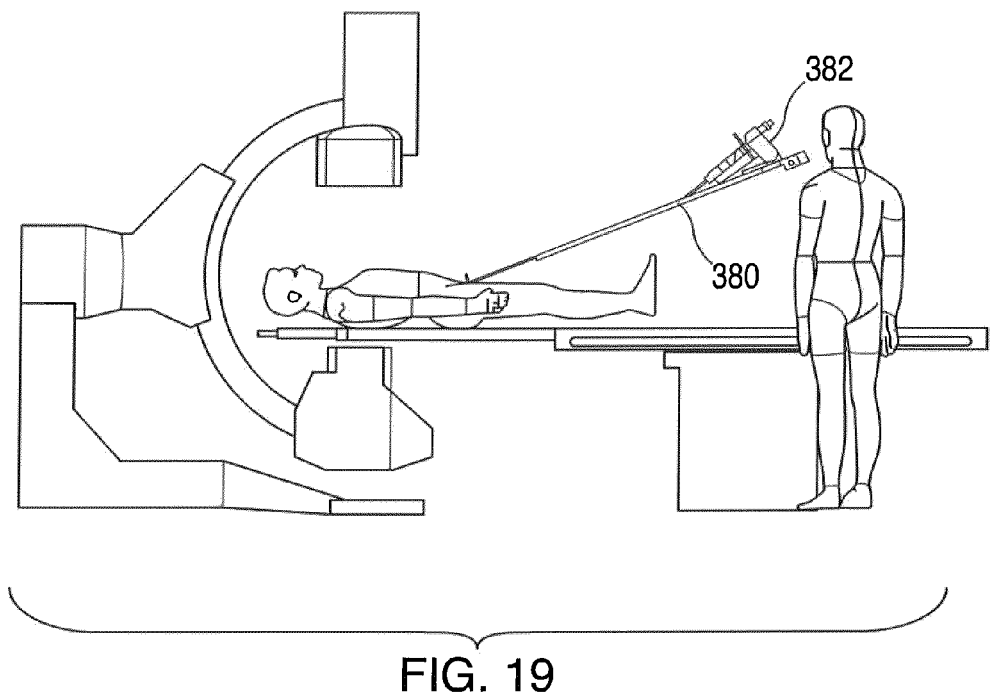
FIG. 19 is a view of the invention and the relative size in working context in accordance with an embodiment of the invention.

FIG. 19 depicts the system in perspective to a patient. Linear sled base 380 is disposed at an angle to a patient, with sled member 382 disposed at an angle to sled base 380.

In another embodiment of the invention, as depicted in FIGS. 21-24, sled base 400 may be mounted onto a bridge or mounting assembly 402 for directing the catheter into a patient. Assembly 402 comprises an elongated plate 404 on which sled bed 400 may be mounted. Elongated plate 404 is preferably comparable in length to sled base 400 to provide adequate support. Elongated plate 404 is mounted on a connector member 406, which is positioned on a rail 408. Connector member 406 can be moved sideways along rail 408 for optimum positioning of the catheter. Connector member 406 is structured and arranged to allow for pivoting of elongated plate 404 about the longitudinal axis of rail 408. Connector member 406 can be manually adjusted or remotely controlled to translate elongated plate 404 horizontally on a plane above a patient situated on a bed 410. Bed 410 may be a padded surface for the patient's comfort and for positioning the patient for insertion of a catheter. Connector member 406 can tilt elongated plate 404 vertically up or down in a lever-like manner in order to better position the catheter. Optionally elongated plate 404 can be rotated in planar fashion on connector member 406 as well.

Figure 21:
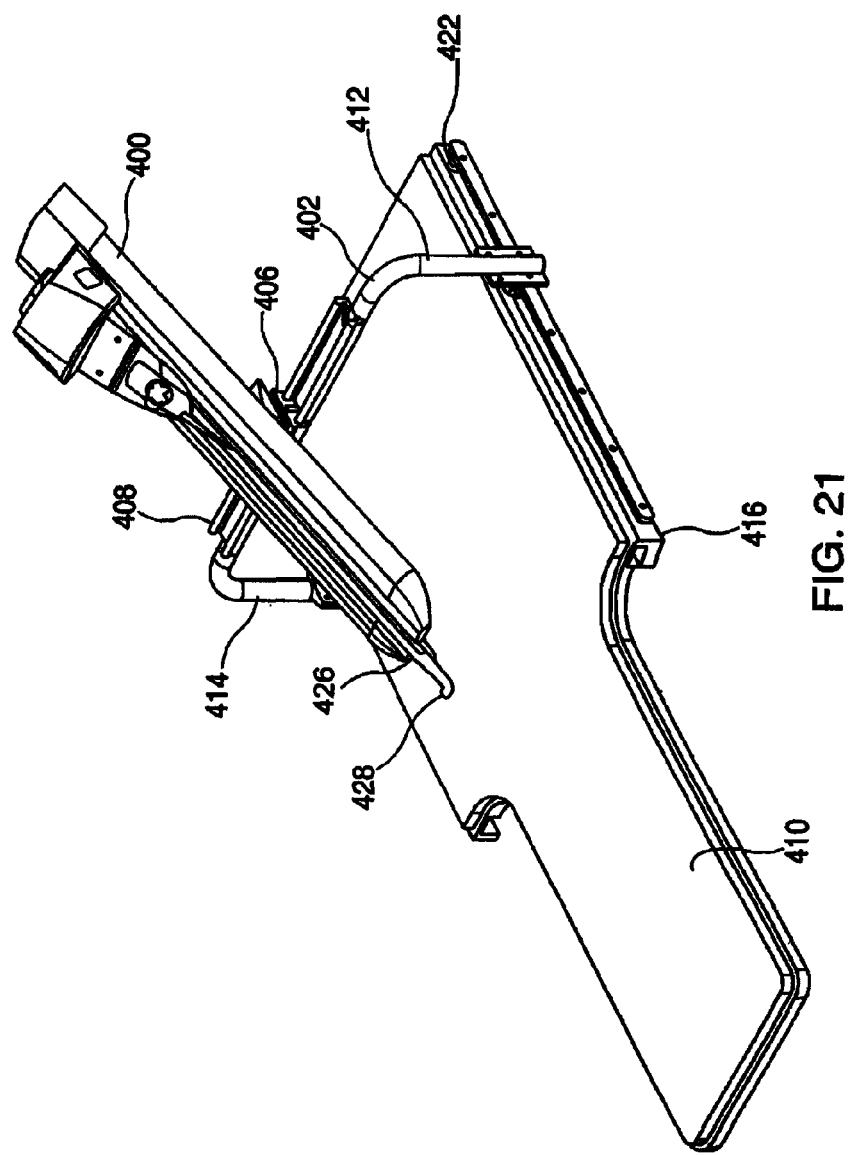
FIG. 21 is top perspective view of a sled member bed connected to the mounting assembly in accordance with an embodiment of the invention.
Figure 22:
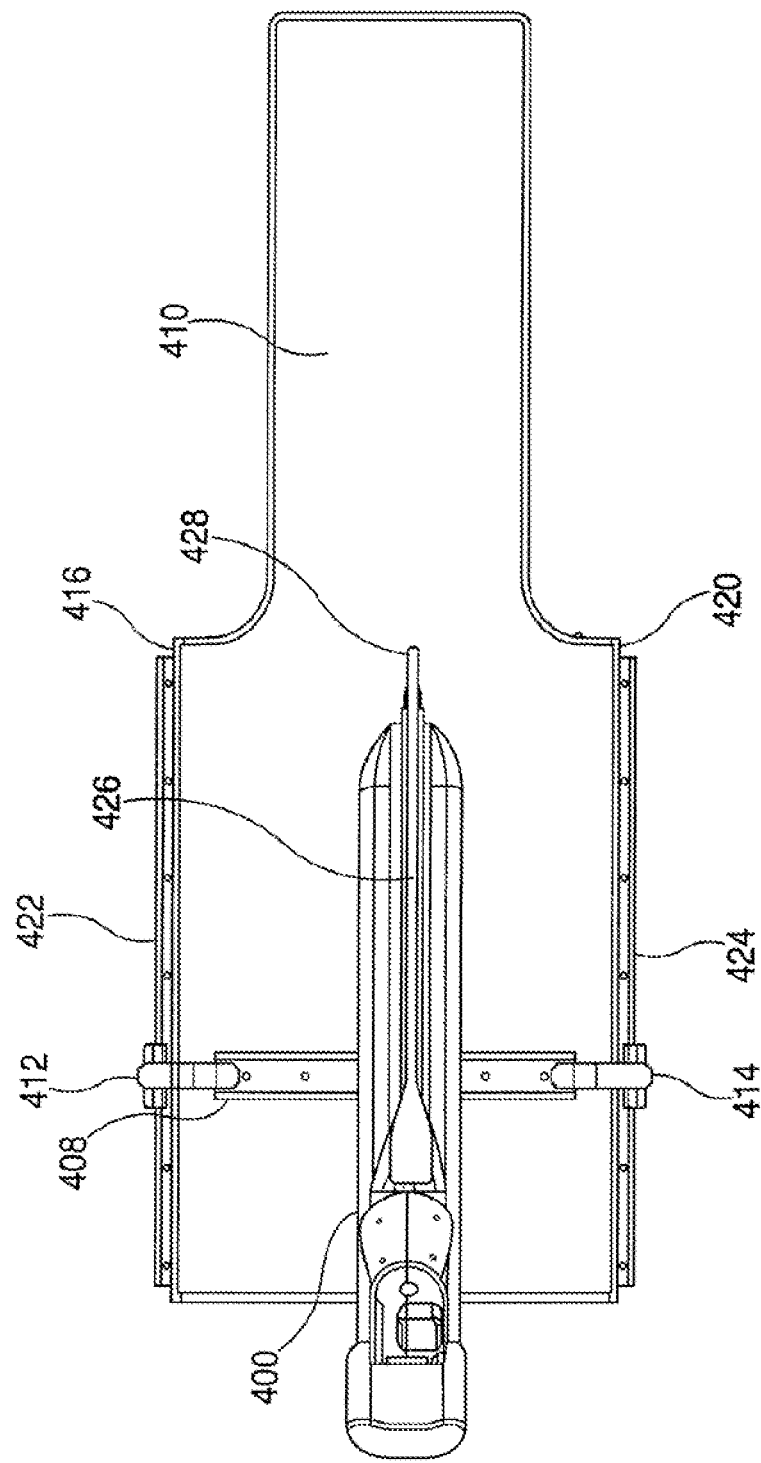
FIG. 22 is a top view of the embodiment of FIG. 21.
Figure 24:
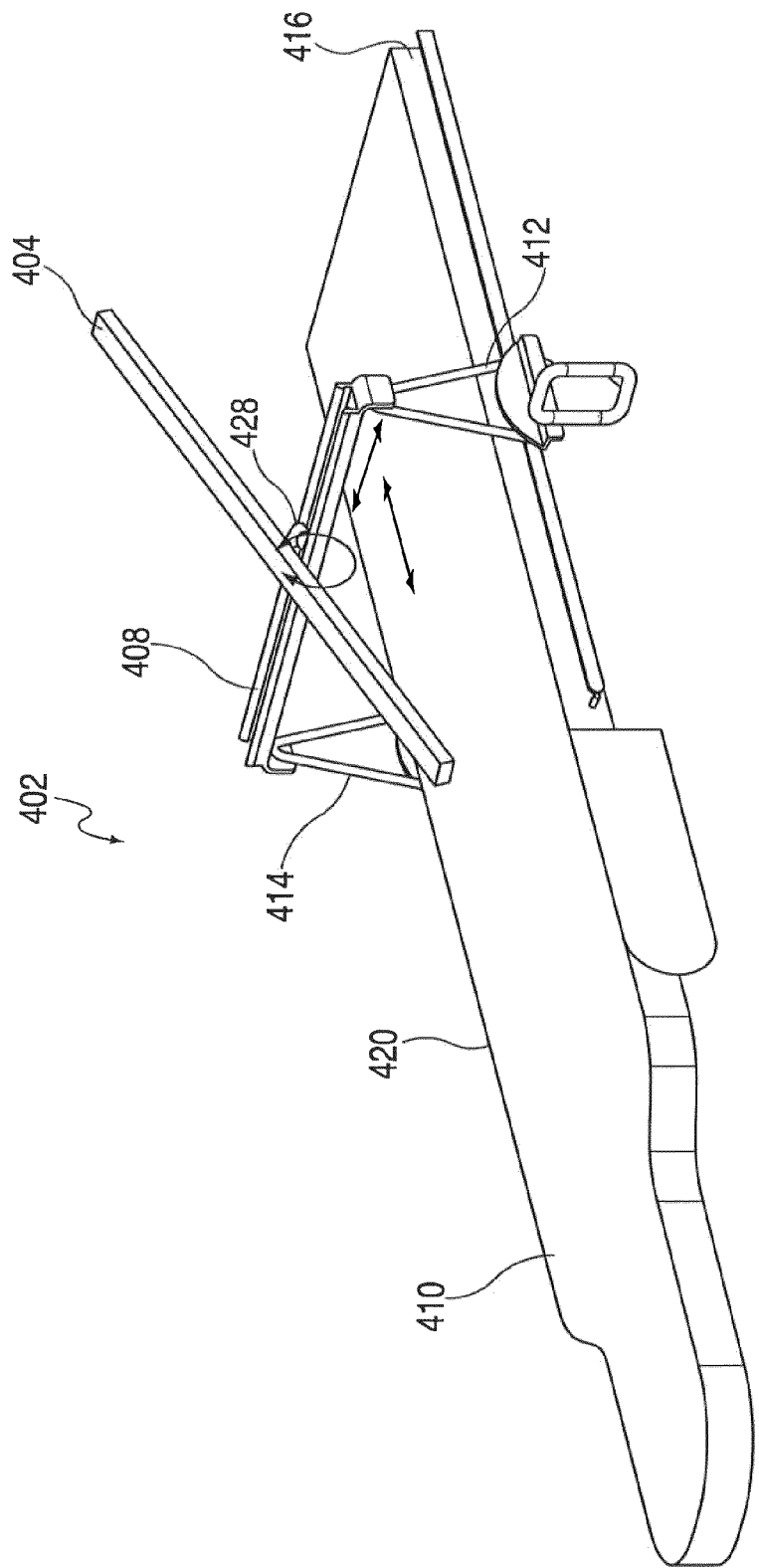
FIG. 24 is a side perspective view of the frame of the catheter delivery system of the invention.

Rail 408 is mounted on a plane above bed 410 by a pair of mounting members 412 and 414 on opposed sides of bed 410. Mounting members 412 and 414 may be in the shape of an inverted letter "v" as seen in FIG. 24 or may be straight bars as seen in FIG. 21. Side surfaces 416 and 420 of bed 410 have lateral rails 422 and 424, which allow for forward and reverse movement of the mounting assembly 402. Mounting members 412 and 414 are sized to suspend rail 408 at a height above the patient that optimizes guiding of the catheter into the patient's body. The height of mounting members 412 and 414 may be adjusted to accommodate patients of different sizes. Thus, the operator can move the bridge and attached robot forwards and backwards along the table to position the robot. The operator can move the robot in the vertical plane (tilt up/down) and then lock into position. Also, the operator can move the robot in a horizontal plane across the table. The bridge will fix the desired height of the robot, and the bridge will have a brake system to lock in position with regard to the robot and/or the table/rail. Preferably the robot will be easily attached and detached to/from the bridge through a simple lever interlock. The bridge itself will also be easily attached and detached to/from the EP table bed.

An electrical power source (not shown) connected to mounting assembly 402 can provide power for the automated movement of the elongated plate 404 and the connector member 406. Elongated plate 404 and connector member 406 may also be adjusted manually if desired. In addition, an electrical power source or any controls necessary to activate or power an aspect of the system can be mounted remotely (for example, below or on the surface of bed 410) and the wire or cabling can be run through mounting member 412 and/or 414 to sled base 400.

Figure 23:
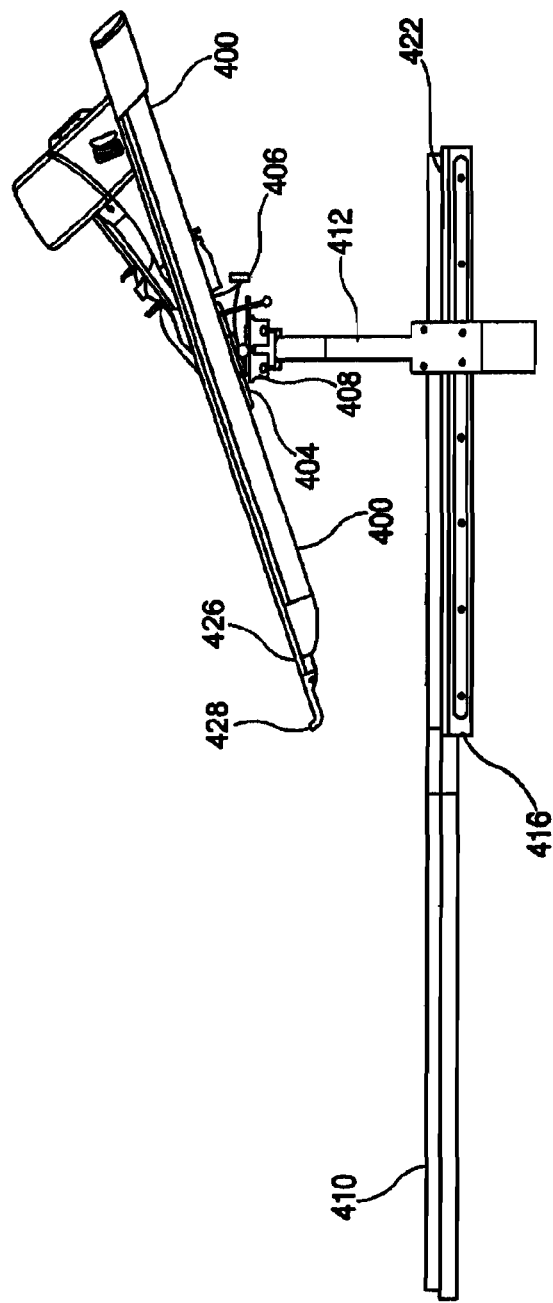
FIG. 23 is a right side view of the embodiment of FIG. 21.

As seen in FIGS. 21 and 23, sheath 426 may have a long preformed curve 428 at its end. The curve 428 is usually placed transeptally into the left atrium and used for atrial fibrillation ablation. Mounting assembly 402 enables the sheath to be moved forward and back and rotated left and right in addition to the deflection provided by sled base 400 as described in more detail below.

In the embodiment of the invention set forth in FIGS. 21 to 24, a single catheter bed sled is shown supported by a bridge support system. It should be appreciated that it is within the scope of the invention that two or more catheter sled beds could be simultaneously supported by a bridge support system. There could be sled beds for one or two catheters and one or two sheaths or other medical devices. For example, there could be one catheter sled bed for an ablation catheter and one catheter sled bed for a mapping and/or ultrasound catheter. In a situation where there is more than one sled bed but a single handle controller, there would preferably be a switch mechanism so that the operator could remotely drive more than one robot. This handle controller would need to clearly have an indicator and switching mechanism which would let the operator know which catheter is being remotely manipulated. In addition, there could be of more than one handle controller (each geared to a particular catheter) and each could be specifically designed for the particular catheter.

In one embodiment of the invention, a sleeve or curtain can be removably affixed, for example, with a VELCRO® adhesive system, to the lateral surfaces or edges of bed 410 to prevent feet from kicking the bridge and/or robot or any of the controls or control wires.

Thus, by utilizing conventional, commercially available catheters, a more adaptable and inexpensive remotely controlled catheter insertion system is realized. As standard catheters are used, and catheters are the only instruments which would be inserted into a subject, no additional governmental approval may be needed. As a modular handle is used, catheters of various sizes, shapes and manufacturers can all be incorporated into the system. Technicians can easily adapt to use of the controller as familiar controls and screens are available and viewed by the technician.

The described system is safe due to many features. For example, the motor effective to move a catheter forward and backward may ultimately apply less force than is available through a human hand and therefore there is less concern for perforation. Such force can be sensed through various sensors so as to ensure that excessive force is not applied such as through the stabilizer bar. Similarly, sensors can be applied to detect the amount of clockwise and counter-clockwise movement and movement of the gears facilitating deflection of the distal end of the catheter. Use of all this sensor data may ensure a safe system. In addition, certain limits, cut-offs, etc., could provide a level of safety even beyond that of a manually performed procedure.

Any type of catheter could be used, such as a diagnostic or angiographic catheter, or catheters including various types of pumps, stylets, guide wires or balloons. Specifically, the modular plate, which attaches to the sled member and handle controller, may be adapted to any type of catheter on the market. Different modular plates may be purchased depending upon the catheters to be used in a procedure.

Positions of the catheter may be maintained even if power is shut off. For example, all six ranges of motion are not dependent upon continuous power supply. For example, a particular deflection may be set and then the deflection motor may be turned off while the rotation motor is applied. Similarly, a continuous radio frequency ablation treatment may be implemented for a particular deflection angle while the catheter is remotely pulled back to create a linear ablation. Some types of treatments include microwave, ultrasound, radiofrequency, cryoablation, chemical ablation, delivery of biologics, etc. Conventional non-fluoroscopic three-dimensional mapping can be used to track catheter movement and ablation applications.

While prior art controllers required a user to learn a new control scheme, embodiments rely on control schemes known by users and generally taught in school.

The position of the catheter can be measured and recorded using fluoroscopy and/or 3D mapping systems. Using a computer program and feedback system the robotic device could automatically or semi-automatically manipulate the catheter to position and place the catheter according to the operator's specifications. Software programs using feedback from the catheter system with appropriate fail-safes could manipulate and perform catheter ablations in precise targeted locations without the operator necessarily remotely moving the catheter. The operator could monitor the automatic and targeted operations and could shut off the system if there is any deviation from a planned and targeted mapping/ablation procedure. A software program can analyze, through the sensors, the movements of each of the motors and/or gears for particular placement of a catheter inside a subject. For example, a technician may first perform a procedure while software is analyzing the movements of each of the motors. Thereafter the software may be used as a supplement to the control station so as to robotically control a catheter to a particular location and/or perform a particular procedure. Such a function is particularly helpful in situations where certain procedures need to be repeated multiple times. In addition, the computer software could perform a series of iterative movements of the catheter towards a three-dimensional target, eventually focusing in on the target. The software program can learn from said movements, return to certain locations, or perform a series of maneuvers (possibly drawn or targeted on a computer) such as encircling pulmonary veins with ablation applications to achieve pulmonary vein isolation. In addition, cavo-tricuspid isthmus lines can be created to ablate atrial flutter. Finally, scar maps can be created and ablation lines automatically or semi-automatically formed to prevent reentrant ventricular tachycardia from occurring.

The systems as described can be disposed anywhere including being mounted by a boom off of, for example, a ceiling, mounted on a table, or beside or across from a subject. The systems may be mounted and secured firmly to an insertion site so as to translate insertion force without being moved backward. A circular monorail or other configuration of rail would help support one or more robots for the purpose of remote mapping and ablation or one or more catheters. There may be adjustable supports to swing the device in and out of position (when in use and when not in use).

Further, additional backend modules can remotely control manipulation, such as forward/backward motion, rotation, deflection, drug/contrast delivery, balloon inflation, energy/therapy delivery, or stent/device deployment.

In another embodiment of the invention, there are two easy methods to remotely manipulate a standard and inexpensive long sheath with a preformed curve at the end (usually placed transeptal into the left atrium and used for atrial fibrillation ablation) together with the catheter manipulation system described herein. Additionally one could control a long steerable introducer sheath which would also control the distal curvature (i.e., deflection of the sheath) through which the catheter travels. It is possible to modify the catheter manipulation system described herein to allow forward and backward movement of the long sheath, together with rotation left and right of that sheath. The following are two examples of such.

It is desirable to be able to remotely manipulate a long sheath which delivers a catheter into a cardiac chamber. The sheath should be able to remotely be moved forward and back and rotated left and right. Additional methods for control of deflectable sheaths could also be accomplished. The goal is to provide additional degrees of control and manipulation in a standard fashion (except the various embodiments will allow this to be performed remotely) using standard approved introducers (along with standard catheters).

In a first method, the existing sterile inner tram and distal connector to the introducer can be permitted to advance and retract (allowing forward and backward motion of the introducer sheath itself via another motor driver; or a motor driver with a gear switch perhaps). Rotation of the sheath can be accomplished by rotation of the inner tram which connects distally to the introducer sheath or the arm (or a second rotation mechanism).

In a second method, using the system described above, a second driver and mechanism (such as a long screw mechanism, belt or rod which can be contained in the arm with a distal motor driver) can be attached directly to the introducer sheath. Rotation of the introducer itself could be accomplished via a gear, belt, etc., which would apply torque to the introducer while allowing the catheter to be driven through.

Both methods described would allow the catheter to be remotely manipulated in all degrees of freedom as was previously described. However, the additional ability to remotely manipulate a standard long sheath is desirable and is currently being performed nonremotely (i.e., at the bedside with lead worn and fluoroscopy) by many electrophysiologists. With the current system, one would occasionally have to go in the room and manually manipulate the long introducer sheath if extra steerability and control are needed. The method described above would permit remote manipulation of a standard catheter and a standard long sheath separately and together and may be desirable in the near future.

In addition, steerable sheaths which are also being used to a lesser extent could be controlled along with catheters.

In other words, a system according to the invention would allow full remote manipulation of standard catheters together and separately with the remote manipulation of standard long introducer sheaths. Additionally, embodiments may include the ability to remotely control steerable sheaths together and separately with catheters.

While preferred embodiments have been described, the invention is only limited by the scope of the claims.

Those skilled in the art will recognize that the method and system of the present invention has many applications, may be implemented in many manners and, as such, is not to be limited by the preceding and following exemplary embodiments and examples. Additionally, the functionality of the components of the preceding and following embodiments may be implemented in different manners. Further, it is to be understood that the steps in the embodiments may be performed in any suitable order, combined into fewer steps or divided into more steps. Thus, the scope of the present invention "covers" conventionally known and future developed variations and modifications to the system components described herein, as would be understood by those skilled in the art.

We claim:

1. A system for remote positioning within the body of a patient of a catheter having a proximal portion, the system comprising:
    a tele-robotic device comprising:
        a handle controller configured to receive the proximal portion of the catheter;
        a sled member coupled to the handle controller;
        a longitudinally-extending sled base configured to advance the sled member longitudinally along a longitudinally-extending guide towards the body of the patient; and
        a longitudinally-extending sterile barrier positioned on the sled base and comprising a resealable delivery channel configured to receive and guide the catheter, the resealable delivery channel comprising a longitudinally-extending recess dimensioned to accept the catheter and having an opening above the recess comprising a pair of resealable lips configured to provide an entry for the catheter to be pressed into and fed into the recess; and
    a remote controller configured to receive user input commands and send control commands to the tele-robotic device.

2. The system of claim 1, wherein the handle controller comprises a handle control assembly and a modular plate.

3. The system of claim 2, wherein the handle control assembly comprises a molded nest to receive the proximal portion of the catheter.

4. The system of claim 3, wherein each of the handle control assembly, modular plate, and molded nest is disposable or resterilizable.

5. The system of claim 1, wherein the sled member is configured to move along a rail or rails in the sled base.

6. The system of claim 1, wherein the handle controller comprises a rigid or semi-rigid tubular feeder member that directs the catheter into the longitudinally-extending recess through the pair of resealable lips at an angle and minimizes buckling.

7. The system of claim 6, wherein the feeder member has no moving parts, is capable of engaging the handle controller when the proximal portion of catheter is positioned in the handle controller and is capable of disengaging from the handle controller when the proximal portion of the catheter is disengaged from the handle controller, and wherein the feeder member is configured so that it does not interfere with movement of the catheter if the catheter is manipulated manually and the feeder member is capable of re-engaging with the handle controller when the proximal portion of the catheter is re-engaged with the handle controller.

8. The system of claim 3, wherein the tubular feeder member directs the catheter into the longitudinally-extending recess through the pair of resealable lips at an angle.

9. The system of claim 1, further comprising a driver configured to move the sled member forward and backward along the guide.

10. The system of claim 1, wherein the sled base has a distal portion and said distal portion has an introducer member that directs the catheter into the patient and minimizes buckling of the catheter in the vicinity of the patient.

11. The system of claim 10, further comprising a clamp configured to secure the introducer member to the sled base, wherein the clamp is capable of being opened to release the introducer member in a sterile fashion.

12. The system of claim 11, wherein the clamp is adjustable and is capable of adapting to a wide variety of introducer sheaths and catheters of various sizes and configurations.

13. The system of claim 1, wherein the sled base is covered by a sterile system comprising a drape effective to maintain sterility and further effective to permit sterile placement and removal of the catheter for remote manipulation and manual manipulation, respectively, without contamination.

14. The system of claim 1, wherein the remote controller comprises a remote control station configured to control the tele-robotic device from a location that is remote from the patient.

15. The system of claim 1, wherein the remote controller is wireless.

16. The system of claim 1, wherein the remote controller has a look and feel of a handle of the catheter.

17. The system of claim 1, wherein the proximal portion of the catheter comprises a handle and the handle controller is configured to receive and engage the handle.

18. The system of claim 17, wherein the catheter comprises a tip and mechanical features in the handle for deflecting the tip, and wherein the handle controller contains mechanical components which can interact with the mechanical features of the handle of the catheter such that the tip of the catheter can be deflected in response to inputs received on the remote controller.

19. The system of claim 1, wherein the system is configured such that the catheter may be disengaged from the handle controller, the sled member, and the sled base for manual manipulation, and reengaged with the handle controller, the sled member, and the sled base, while maintaining sterility without substantially dislodging the catheter from a targeted region within a patient's body.

20. The system of claim 1, wherein the system is configured such that the distal portion of the catheter is inserted into the patient's body without an encasing.

21. The system of claim 1, further comprising detection sensors in the remote controller configured to detect human contact or presence,
    wherein the system is configured to prevent inadvertent activation of any control or function of the remote controller based on signals received from the detection sensors.

22. The system of claim 21, wherein the detection sensors sense temperature, pressure or infrared radiation.

23. The system of claim 1, wherein the handle controller comprises a deflection wheel.

24. The system of claim 1, wherein a switch on the remote controller can be utilized to switch between controlling the robotic device and one or more additional robotic devices.

25. The system of claim 1, wherein components of the handle controller are designed to manipulate a specific catheter.

26. The system of claim 1, wherein the tele-robotic device is further configured to feed the catheter within the patient's circulatory system.

27. The system of claim 1, wherein the catheter is an ablation catheter.

28. The system of claim 1, wherein the catheter is a mapping catheter.

29. The system of claim 1, wherein the catheter is an intracardiac echo catheter.

30. The system of claim 1, wherein the catheter is an imaging catheter.

31. The system of claim 1, wherein the catheter is a diagnostic catheter.

32. The system of claim 1, wherein the catheter is an interventional treatment catheter.

33. The system of claim 1, wherein the catheter is a drug delivery catheter.

34. The system of claim 1, wherein the catheter is a biologics delivery catheter.

35. The system of claim 1, wherein the catheter includes a lead for pacing, shocking, cardioverting, or defibrillating.

36. The system of claim 35, wherein the tele-robotic device can advance and remove the lead and rotate the lead clockwise and counter-clockwise.

37. The system of claim 36, wherein the lead is configured to be deployed within the coronary sinus vein or its branches.

38. The system of claim 18, further comprising:
a first motor connected to the sled member and effective to at least move the sled member forward and backward;
a second motor connected to the handle controller and effective to at least rotate the catheter;
a third motor connected to the mechanical components of the handle controller and effective to at least drive the mechanical components to deflect the distal end of the catheter in at least a first direction; and
a controller unit connected to the first, second and third motors and configured to receive commands from the remote controller.

39. The system of claim 1, wherein the catheter is a commercially available steerable catheter.

40. The system of claim 1, further comprising:
an elongated plate having a surface adapted for connection to the sled base;
a connector member connected to said elongated plate structured and arranged for manipulating the position of the elongated plate;
a rail for translation of said elongated plate and connector member in at least one dimension; and
a pair of mounting members for mounting said rail onto a planar structure, the mounting members adapted for connection to lateral rails of said planar structure,
wherein said mounting members may be translated in at least one dimension along said lateral rails.

41. The system of claim 40, wherein the elongated plate and connector member can be positioned laterally along the rail and releasably locked in position.

42. The system of claim 40, wherein the elongated plate and connector member can be rotated about the longitudinal axis of the rail and releasably locked in position.

43. The system of claim 40, wherein the elongated plate can be rotated about the connector member and releasably locked in position.

44. The system of claim 1 further comprising a mounting assembly for mounting said tele-robotic device comprising:
an elongated plate having a surface adapted for connection to said tele-robotic device;
a connector member connected to said elongated plate structured and arranged for manipulating the position of the elongated plate;
a rail for translation of said elongated plate in one dimension; and
a pair of mounting members for mounting said rail onto a bed structure, the mounting members adapted for connection to lateral rails of said bed structure, wherein said mounting members are configured to be translated in one dimension along said lateral rails.

45. The system of claim 1, further comprising a circular monorail bridge coupled to the tele-robotic system and configured to be positioned over a table and attached securely to opposite positions on the table, and to be effective to support the tele-robotic system.

* * * * *